US007241776B2

(12) United States Patent
Carroll et al.

(10) Patent No.: US 7,241,776 B2
(45) Date of Patent: Jul. 10, 2007

(54) CYANOAMIDINE P2X$_7$ ANTAGONISTS FOR THE TREATMENT OF PAIN

(75) Inventors: William A. Carroll, Evanston, IL (US); Arturo Perez-Medrano, Grayslake, IL (US); Sridhar Peddi, Grayslake, IL (US); Alan S. Florjancic, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 523 days.

(21) Appl. No.: 10/909,502

(22) Filed: Aug. 2, 2004

(65) Prior Publication Data
US 2006/0025614 A1 Feb. 2, 2006

(51) Int. Cl.
*A61K 31/47* (2006.01)
*A61K 31/381* (2006.01)
*C07D 215/00* (2006.01)
*C07D 333/02* (2006.01)

(52) U.S. Cl. ...................... 514/311; 546/112; 546/152; 546/174; 546/175; 546/329; 546/334; 549/29; 549/74; 549/76; 558/303; 558/388; 558/390; 558/392; 514/438

(58) Field of Classification Search ................ 546/112, 546/152, 174, 175, 329, 334; 549/29, 74, 549/76; 514/311, 438; 558/390, 392
See application file for complete search history.

(56) References Cited

U.S. PATENT DOCUMENTS

| 5,380,734 | A | 1/1995 | Hsu et al. |
| 2003/0004513 | A1 | 1/2003 | Guzman et al. |
| 2003/0187031 | A1 | 10/2003 | Alcaraz et al. |

FOREIGN PATENT DOCUMENTS

| EP | 0 412 531 | 2/1991 |
| EP | 0 934 941 | 8/1999 |
| JP | 04 295473 | 10/1992 |
| WO | 91/04965 | 4/1991 |
| WO | 92/06978 | 4/1992 |
| WO | 93/15055 | 8/1993 |
| WO | 95/31448 | 11/1995 |

OTHER PUBLICATIONS

Kiriyama, Kazuhisa, et al., "Insecticidal and neuroblocking activities of acetamiprid and related compounds", XP002355181, retrieved from STN Database accession No. 2003:341680 abstract.
Kupchik, E.J. and Hanke, H.E., "Reactions of Thioamides with Bis(triphenylstannyl) carbodiimide and (Triphenylstannyl) Cyanamide", Journal of Organometallic Chemistry, vol. 97, pp. 39-44, 1975.
Mase, Toshiyasu, et al., "Preparation of pyridylpyrrolothiazole derivatives as platelet activating factor (PAF) antagonists", XP002355182, retrieved from STN Database accession No. 1992:255603 abstract.

Anderson C., et al., "ATP-Activated Glutamate Release through Non-Selective P2Z/P2X7 Like Channels in Cultured Mouse Astrocytes", Drug Dev. Res., Abstracts from Purines 2000, Sec. 177, vol. 50, pp. 92 (2000).
G. Dell'Antonio, "Antinociceptive effect of a new P$_{2z}$/P2X7 antagonist, oxidized ATP, in arthritic rats", Neuroscience Letters 327, pp. 87-90 (2002).
S.M. Berge, et al., "Pharmaceutical Salts", J. Pharmaceutical Sciences, vol. 66, No. 1, pp. 1-19 (1977).
Bianchi, et al., Pharmacological characterization of recombinant human and rat P2X receptor subtypes , European. Journal of Pharmacol. vol. 376, pp. 127-138 (1999).
Blanchette et al., "The Willgerodt Reaction in the Heterocyclic Series. II. Temperature Studies with Thienyl Ketones", Journal of Amer. Chem. Soc., vol. 74, p. 1066-1067 (1952).
Brough, D., et al., "Purinergic (P2X7) Receptor Activation of Microglia Induces Cell Death via an Interleukin-1-Independent Mechanism", Molecular and Cellular Neuroscience, vol. 19, pp. 272-280 (2002).
Collo, G., "Tissue Distribution of the P2X$_7$ Receptor", Neuropharmacology, vol. 36, No. 9, pp. 1277-1283, (1997).
De Tar, et al., "The Willgerodt Reaction. II. A Study of Reaction Conditions with Acetophenone and Other Ketones", J. Amer. Chem. Soc., vol. 68, pp. 2025-2028 (1946).
Deuchars, Susan, et al., "Neuronal P2X$_7$ Receptors are Targeted to Presynaptic Terminals in the Central and Peripheral Nervous Systems", The Journal of Neuroscience, vol. 21(18), pp. 7143-7152, (Sep. 15, 2001).
Dixon, Ann., "Efficient Analysis of Experimental Observations", Rev. Pharmacol. Toxicol., vol. 20, pp. 441-462 (1980).
Edwards, M. and Williams, "Catalytic Electronic Activation: Indirect "Wittig" Reaction of Alcohols", J., Angewandte Chemie, Intl. Edition vol. 41 (24), pp. 4740-4743 (2002).
Engler, T.A., "An improved method for direct conversion of heteroaryl-aldehydes to heteroaryl-acetonitriles", Tetrahedron Letters, vol. 44 (14), pp. 2903-2905 (2003).

(Continued)

*Primary Examiner*—Golam M. M. Shameem
(74) *Attorney, Agent, or Firm*—Gabryleda Ferrari-Dileo

(57) ABSTRACT

Novel cyanoamidines compounds of formula (I) and (II)

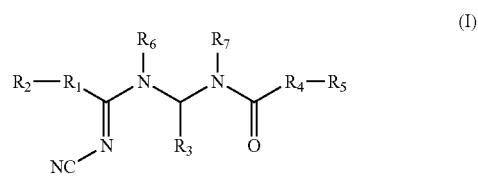

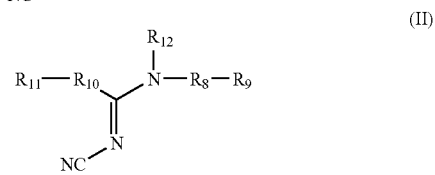

and their derivatives wherein $R_1$-$R_{12}$ are as defined in the specification act as antagonists of the P2X$_7$ receptor. These compounds are particularly useful in the treatment of pain, inflammation and neurodegeneration states.

22 Claims, No Drawings

OTHER PUBLICATIONS

Ganellin, C. Robin, et al., "Synthesis of Potent Non-imidazole Histamine H3-Receptor Antagonists", Arch. Pharm. Pharm. Med. Chem. , vol. 331, pp. 395-404 (1998).

Hatcher, Jonathan, et al., "Disruption of the P2X7 Purinoceptor Gene Abolishes Chronic Inflammatory and Neuropathic Pain", (6th Intl. Conf. On the Mechanisms and Treatment of Neuropathic Pain, San Francisco, CA (Sep. 18-20, 2003) GlaxoSmithKline, Dept. of Pain Research, Neurology & Gastroenterology CEDD.

T. Higuchi and V. Stella (Editors), Pro-Drugs as Novel Delivery Systems, V. 14 of the A.C.S. Symposium Series, (1975).

Humphrey BD and Dubyak GR, "Induction of the $P2z/P2X_7$ Nucleotide Receptor and Associated Phospholipase D Activity by Lipopolysaccharide and IFN-γ in the Human THP-1 Monocytic Cell Line", J. Immunology, vol. 157 pp. 5627-5637 (1996).

Jacobson, K.A., et al., "Adenosine and Adenine Nucleotides: From Molecular Biology to Integrative Physiology", L. Belardinelli and A. Pelleg (eds.) pp. 149-166 (1995).

Kelley, James L., et al., 8-Amino-3-benzyl-1,22,4-triazolo[4,3-a] pyrazines. Synthesis and Anticonvulsant Activity, Journal of Medicinal Chemistry, vol. 38, (18), pp. 3676-3679 (1995).

Kim, Sun Ho and Chung, Jin Mo, "An experimental model for peripheral neuropathy produced by segmental spinal nerve ligation in the rat", Pain, vol. 50, pp. 355-363 (1992).

Mayer, Joachim M., et al., Structural Factors Affecting the Basicity of w-Pyridylallkanols; w-Pyridylalkanamides and w-Pyridylalkylamines, Helvetica Chimica Acta, vol. 65, pp. 1868-1884 (1982).

Meyer, M.D., et al., Structure-Activity Studies for a Novel Series of N-(Arylethyl)-N(1',2,3,4-tetrahydronaphthalen-1-ylmethyl)-N-methylamines Possessing dual 5-HT Uptake Inhibiting and a2-Antagonistic Activities, Journal of Med. Chem., vol. 40, No. 7, pp. 1049-1062 (1997).

Moehrle, H., et al., Chemical Sciences, vol. 53(11), pp. 1369-1378 (1998).

Perretti M., et al., "Evidence that endogenous interleukin-1 is involved in leukocyte migration in acute experimental infglammation in rats and mice", Agents Actions, vol. 35 (1-2), pp. 71-78 (1992).

Edward B. Roche, (Editor)., Bioreversible Carriers in Drug Design, American Pharmaceutical Association and Pergamon Press (1987).

Ruechardt, et al., "Die Zerfallsgeschwindigkeit des p-Methylmercapto-phenylperessigsaure-tert.-butylesters", Chem. Ber., vol. 100, p. 654 (1967).

Sato, Y., et al., "Syntheses of 2-hydroxymethylnicotinic Acid Lactone, 2-Hydroxymethylpyridine-3-acetic Acid Lactone, and Sope of their Derivatives", Chem. Pharm. Bull., vol. 8, pp. 427-435 (1960).

Torok K., et al., "Measurement and drug induced modulation of interleukin-1 level during zymosan peritonitis in mice", Inflamm. Res. vol. 44 (6) pp. 248-252 (1995).

Tsatsaronis, G.C., "Synthesis of 4,5-Disubstituted Pyrimidines", Journal of Org. Chem., vol. 35, No. 2, p. 438-441 (1970).

Verhoef, Philip A., "P2X7 Receptor-Dependent Blebbing and the Activation of Rho-Effector Kinases, Caspases, and IL-1Beta Release[1]", The Journal of Immunology, vol. 170, pp. 5728-5738 (2003).

Wagner, G. and Vieweg, H., "Synthese von Amidinochinolinen und Amidinochinolonen-(4)", Pharmazie, vol. 31, pp. 145-148 (1976).

Wang, X., et al., "P2X7 receptor inhibition improves recovery after spinal cord injury", Nature Medicine, vol. 10, No. 8, pp. 821-827 (Aug. 2004).

Weintraub, L., et al., "A convenient General Synthesis of Amidines", J. Org. Chem., vol. 33(4), pp. 1679-1681 (Apr. 1968).

1

CYANOAMIDINE P2X$_7$ ANTAGONISTS FOR THE TREATMENT OF PAIN

TECHNICAL FIELD

The present invention relates to cyanoamidines of formula (I) and (II) that are P2X$_7$ antagonists and are useful for treating pain, inflammation and neurodegeneration states.

BACKGROUND OF THE INVENTION

P2X receptors are ionotropic receptors activated by ATP. The importance of P2X receptors in nociception is underscored by the variety of pain states in which this endogenous ligand can be released. Of the seven P2X receptors, the P2X$_7$ is distinguished by its ability to form a large pore upon prolonged or repeated agonist stimulation. It is partially activated by saturating concentrations of ATP, whereas it is fully activated by the synthetic ATP analog benzoylbenzoic ATP (BzATP) (Bianchi et al., *Eur. J. Pharmacol. Vol.* 376, pages 127-138, 1999). The P2X$_7$ receptor is expressed by presynaptic terminals in the central and peripheral nervous systems, antigen-presenting cells including macrophages, human epidermal Langerhans' cells, microglial cells and a number of tumor cell lines of varying origin (Jacobson K A, et al. "*Adenosine and Adenine Nucleotides: From Molecular Biology to Integrative Physiology*". L. Belardinelli and A. Pelleg (eds.), Kluwer, Boston, pages 149-166, 1995).

On glial cells, the P2X$_7$ receptor has been shown to mediate release of glutamate (Anderson C. et al., *Drug Dev. Res. Vol.* 50 page 92, 2000). Since glutamate is known to be involved in the neurotransmission of painful sensory signals, inhibition of P2X$_7$ may have therapeutic utility in the treatment of various pain states. Furthermore, oxidized ATP (oATP), a nonselective and irreversible P2X$_7$ antagonist, was recently reported to possess peripherally-mediated antinociceptive properties in inflamed rats (Dell'Antonio et al., *Neuroscience Lett., Vol.* 327, pages 87-90, 2002). Thus, P2X$_7$ antagonists may have utility in the treatment of a variety of pain states.

Recent data also suggested a possible role for P2X$_7$ receptor activation in neuroinflammation and neurodegeneration (Collo G. et al., *Neuropharmacology Vol.* 36, pages 1277-1283, 1997). In the central nervous system, the P2X$_7$ receptor is predominately expressed by microglia, the resident macrophages of the brain. Upregulation of the P2X$_7$ receptor, most likely on activated microglia, was reported at the site of cerebral ischemic damage following middle cerebral artery occlusion in rat brain. Thus, P2X$_7$ antagonists may have utility in the treatment of neurodegenerative conditions including stroke and Alzheimer's disease.

Activation of the P2X$_7$ receptor on cells of the immune system (macrophages, mast cells and lymphocytes) leads to release of interleukin-1β (IL-1β), giant cell formation, degranulation, and L-selectin shedding. Compounds acting at the P2X$_7$ receptor may therefore have utility in the treatment of various disease states and conditions such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischemic heart disease, stroke and varicose veins.

Neuropathic pain is another type of pain different from pain involved with inflammatory or neurodegenerative conditions. Neuropathic pain is associated with any disorder affecting any segment of the nervous system. Common causes of neuropathic pain are, among others, alcoholism, amputation, cancer chemotherapy, diabetes, trigeminal neuralgia, HIV infection, multiple sclerosis, shingles and spine surgery. One of the most dramatic examples of neuropathic pain is called "phantom limb syndrome" which occurs when an arm or a leg have been removed, but the brain still gets pain messages from the missing limb.

A recent study reported the localization of P2X$_7$ on presynaptic terminals in the central and peripheral nervous systems (Deuchars et al., *J. Neuroscience Vol.* 21 pages 7143-7152, 2001) where its activation was linked to release of the excitatory amino acid neurotransmitter glutamate. A recent report suggests a link between a P2X$_7$ purinoceptor gene and chronic, inflammatory and neuropathic pain (Hatcher et al., The 6th International Conference on the Mechanisms and Treatment of Neuropathic Pain. San Fransisco, Calif.—Sep. 18-20, 2003).

Overall, these findings indicate a role for the P2X$_7$ receptor in the process of neuronal synaptic transmission and therefore a potential role for P2X$_7$ antagonists as novel therapeutic tool to treat neuropathic pain.

In view of the above facts, there is a need for P2X$_7$ antagonist that can be efficiently used in treating neuropathic pain, chronic inflammatory pain, inflammation, and neurodegenerative conditions (e.g. Alzheimer's disease).

SUMMARY OF THE INVENTION

The present invention discloses novel cyanoamidine compounds that are P2X$_7$ antagonists, a method of treating pain, inflammation and neurodegeneration states, and pharmaceutical compositions including these compounds. More particularly, the present invention is directed to a compound having formula I,

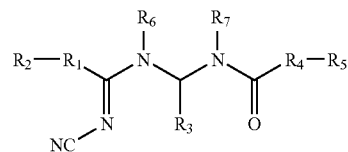

or a pharmaceutically acceptable salt or prodrug thereof, wherein

R$_1$ is a bond or a chain selected from the group consisting of alkyl, alkenyl, and alkynyl, R$_2$ is selected from the group consisting of substituted or unsubstituted aryl and heteroaryl, R$_3$ is selected from the group consisting of alkyl and haloalkyl, R$_4$ is alkyl, R$_5$ is selected from the group consisting of halogen, aryl, and heteroaryl, and $R_6$ and $R_7$ are independently selected from the group consisting of hydrogen and alkyl; and to a compound having formula II,

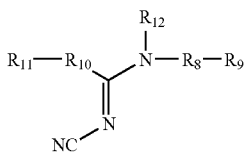

or a pharmaceutically acceptable salt or prodrug thereof, wherein $R_8$ is a bond or a carbon chain selected from the group consisting of alkyl, alkenyl, and alkynyl, $R_9$ is selected from the group consisting of aryl and heteroaryl, $R_{10}$ is a bond or a carbon chain selected from the group consisting of alkyl, alkenyl, and alkynyl, $R_{11}$ is selected from the group consisting of aryl and heteroaryl, and $R_{12}$ is selected from the group consisting of hydrogen and alkyl; alternatively, $R_{12}$ and $R_8$ together with the nitrogen to which they are attached form a 4, 5, or 6 membered heterocycle ring, or when $R_9$ is aryl, $R_{12}$ along with any available carbon atom of $R_9$ form a 5 or 6 membered heterocycle ring, with the proviso that when $R_{11}$ is unsubstituted aryl or aryl substituted with 0, 1, 2, 3 or 4 halogen, and $R_{12}$ is selected from the group consisting hydrogen and alkyl, then $R_9$ is not substituted pyridinyl.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

(a) Definition of Terms

As used throughout this specification and the appended claims, the following terms have the following meanings.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 1-ethylpropyl, 2,2-dimethylpentyl, 2,3-dimethylpentyl, n-heptyl, n-octyl, n-nonyl, n-decyl, and the like.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, refers to a phenyl group, or a bicyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Representative examples of aryl groups include, but not limited to, indanyl (2,3-dihydro-indenyl), indenyl, naphthalenyl, phenyl and tetrahydronaphthalenyl. The aryl groups of the present invention can be connected to the parent molecular moiety through any substitutable carbon atom of the group. The aryl groups of the present invention can be substituted with 0, 1, 2, 3 or 4 substituents independently selected from the group consisting of alkenyl, —ORa, —C(O)ORa, alkylC(O)ORa, alkyl, —C(O)Ra, alkylORa, —OC(O)Ra, alkylOC(O)Ra, —SRa, —S(O)Ra, —S(O)$_2$Ra, —S(O)$_2$RaRb, alkynyl, —C(O)NRaRb, cyano, ethylenedioxy, furyl, halo, haloalkyl, haloalkoxy, imidazolyl, isothiazolyl, isoxazolyl, methylenedioxy, naphthyl, nitro, —NRaRb, alkylNRaRb, —N(Ra)C(O)ORb, —N(Ra)C(O)NRaRb, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl, wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl may be substituted with 1 or 2 substituents independently selected from alkenyl, —ORa, —C(O)ORa, alkylC(O)ORa, alkyl, —C(O)Ra, —OC(O)Ra, alkylOC(O)Ra, —S(O)Ra, —S(O)$_2$Ra, —S(O)$_2$NRaRb, alkynyl, —C(O)NRaRb, cyano, halo, haloalkyl, haloalkoxy, nitro, —NRaRb, and (NRaRb)alkyl, wherein Ra and Rb are independently selected from the group consisting of hydrogen, alkyl, aryl, haloalkyl and arylalkyl. The bicyclic aryl ring systems as defined herein may have two of the non-adjacent carbon atoms connected by an alkylene bridge between one and three additional carbon atoms. Representative examples of bicyclic aryl ring systems that contain such connection between two non-adjacent carbon atoms include, but not limited to, 1,2,3,4-tetrahydro-1,4-methanonaphthalenyl. The phenyl and bicyclic aryl ring systems are connected to the parent molecular moiety through any substitutable carbon atom of the system.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 1,1-dimethyl-2-phenylethyl, 3-phenylpropyl, 2-naphth-2-ylethyl, and the like.

The term "cyano," as used herein, refers to a —CN group.

The term "cycloalkyl," as used herein, refers to a saturated, monocyclic hydrocarbon ring system having three to eight carbon atoms and zero heteroatom. Examples of monocyclic ring systems include cyclopropyl, cyclobutyl, cyclopentyl, cyclohexyl, cycloheptyl, and cyclooctyl.

The term "cycloalkenyl," as used herein, refers to a non-aromatic, partially unsaturated, monocyclic, hydrocarbon ring system, having four to seven carbon atoms and zero heteroatom. The four-, five-, and six-membered rings have one or two double bonds, the seven-membered rings have one, two or three double bonds. Representative examples of cycloalkenyl groups include, but not limited to, cyclobutenyl, cyclopentenyl, and cyclohexenyl.

The term "ethylenedioxy" as used herein, refers to a —O(CH$_2$)$_2$O— group wherein the oxygen atoms of the ethylenedioxy group are attached to the parent molecular moiety through two adjacent carbon atoms of the parent molecular moiety, forming a six membered ring.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, trichloromethyl, 1,1-dichloroethyl, 2-fluoroethyl, trifluoromethyl, 2,2,2-trifluoroethyl, 2,2,2-trifluoro-1-(trifluoromethyl)-1-(methyl)ethyl, pentafluoroethyl, 2-chloro-3-fluoropentyl, and the like.

The term "haloalkoxy," as used herein, refers to at least one halogen, as defined herein, appended to the parent molecular moiety through an alkoxy group, as defined herein.

The term "heteroaryl," as used herein, means an aromatic monocyclic ring or an aromatic bicyclic ring. The aromatic monocyclic rings are five or six membered rings containing 1, 2, 3, or 4 heteroatoms independently selected from the group consisting of N, O, and S. The nitrogen heteroatoms can be optionally quaternized or oxidized to the N-oxide. The nitrogen containing rings can be optionally N-protected. The five membered aromatic monocyclic rings have two double bonds and the six membered aromatic monocyclic rings have three double bonds. The aromatic bicyclic rings are composed of an aromatic monocyclic ring fused to a phenyl group. Alternatively, aromatic bicyclic rings are composed of an aromatic monocyclic ring fused to another aromatic monocyclic ring. The aromatic monocyclic rings and the aromatic bicyclic rings are connected to the parent molecular moiety through a carbon or nitrogen atom. Representative examples of heteroaryl include, but are not limited to, benzothienyl, benzoxadiazolyl, cinnolinyl, dibenzofuranyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyridinium N-oxide, pyrrolyl, quinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, —ORa, alkylORa, —C(O)ORa, alkyl, —C(O)Ra, —OC(O)Ra, —SRa, alkynyl, —C(O)O—, cyano, formyl, haloalkoxy, haloalkyl, halogen, hydroxy, hydroxyalkyl, mercapto, nitro, —NR$_c$R$_c$, and (NR$_c$R$_d$)carbonyl, wherein Rc and Rd are independently selected from hydrogen, alkyl, —C(O)Ra, formyl, aryl and arylalkyl. Representative examples include, but are not limited to, 3-cyanopyridin-2-yl, 5-hydroxypyridin-2-yl, and 3-methylpyridin-2-yl.

The term "heterocycle" as used herein, refers to a monocyclic or bicyclic, non-aromatic, saturated or partially unsaturated ring system. Monocyclic ring systems are exemplified by any 4-membered ring containing a heteroatom independently selected from oxygen, nitrogen and sulfur; or a 5-, 6-, 7-, or 8-membered ring containing one, two or three heteroatoms wherein the heteroatoms are independently selected from nitrogen, oxygen and sulfur. The 5-membered ring has 0 or 1 double bond. The 6-memebered ring has 0, 1 or 2 double bonds. The 7- or 8-membered ring has 0, 1, 2 or 3 double bonds. Representative examples of monocyclic ring systems include, but are not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidyl, pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include but are not limited to, benzodioxinyl, benzopyranyl, benzothiopyranyl, 2,3-dihydroindolyl, indolizinyl, pyranopyridinyl, tetrahydroisoquinolinyl, tetrahydroquinolinyl, thiopyranopyridinyl, 2-oxo-1,3-benzoxazolyl, 3-oxo-benzoxazinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic or bicyclic ring systems as defined herein may have two of the non-adjacent carbon atoms connected by a heteroatom selected from nitrogen, oxygen or sulfur, or an alkylene bridge between one and three additional carbon atoms. Representative examples of monocyclic or bicyclic ring systems that contain such connection between two non-adjacent carbon atoms include, but not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 3-oxa-8-azabicyclo[3.2.1]octyl, 1,4-diazabicyclo[3.2.2]nonyl, 1,4-diazatricyclo[4.3.1.1$^{3,8}$] undecyl, 3,10-diazabicyclo[4.3.1]decyl, or 8-oxa-3-azabicyclo[3.2.1]octyl, octahydro-1H-4,7-methanoisoindolyl, and octahydro-1H-4,7-epoxyisoindolyl.

The heterocycle groups of this invention, including the representative examples listed above, can be optionally substituted with 1, 2, or 3 substituents independently selected from alkenyl, —ORa, —C(O)ORa, -alkylC(O)ORa, alkyl, —CORa, —OC(O)Ra, alkylOC(O)Ra, —S(O) Ra, —S(O)$_2$Ra, —S(O)$_2$NRaRb, alkynyl, —C(O)NRaRb, cyano, halo, haloalkyl, haloalkoxy, nitro, —NRaRb, and (NRaRb)alkyl, wherein Ra and Rb are independently selected from the group consisting of hydrogen, alkyl, aryl, haloalkyl and arylalkyl; furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl may be substituted with 1 or 2 substituents independently selected from alkenyl, —ORa, —C(O)ORa, alkylC(O)ORa, alkyl, —CORa, —OC(O)Ra, alkylOC(O)Ra, —S(O)Ra, —SO$_2$Ra, —SO$_2$NRaRb, alkynyl, —C(O)NRaRb, cyano, halo, haloalkyl, haloalkoxy, nitro, —NRaRb, and (NRaRb)alkyl, wherein Ra and Rb are independently selected from the group consisting of hydrogen, alkyl, aryl, haloalkyl and arylalkyl. The heterocycle groups of this invention are connected to the parent molecular moiety through any substitutable carbon or nitrogen atom in the groups. The nitrogen heteroatom may or may not be quaternized, and may or may not be oxidized to the N-oxide. In addition, the nitrogen containing heterocyclic rings may or may not be N-protected.

The term "hydroxyalkyl" as used herein means at least one hydroxy group as defined herein, appended to the parent molecular moiety through an alkyl group, as defined herein.

The term "methylenedioxy" as used herein, refers to a —O—CH$_2$—O— group wherein the oxygen atoms of the ethylenedioxy group are attached to the parent molecular moiety through two adjacent carbon atoms of the parent molecular moiety, forming a five membered ring.

The term "nitro" as used herein, means a —NO$_2$ group.

(b) Embodiments of the Invention

In its principal embodiment, the present invention discloses a method for treating neuropathic pain in a mammal comprising administering to the mammal a compound having formula (I)

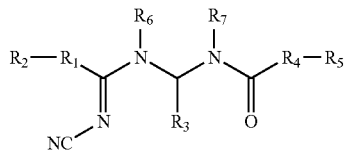

or a pharmaceutically acceptable salt or prodrug thereof, in which $R_1$ is a bond or a chain selected from the group consisting of alkyl, alkenyl, and alkynyl; $R_2$ is selected from the group consisting of aryl and heteroaryl, wherein aryl and heteroaryl can be independently substituted with 0, 1, 2, or 3 alkenyl, alkyl, alkynyl, halo, haloalkyl, nitro, —C(O)—N—RaRb, —C(O)O—Ra, —C(O)—Ra, —N—RaRb, alkyl-N—RaRb, —O—Ra, —OC(O)—Ra, alkyl-O—Ra, —N—(Ra)—C(O)O—Rb, —N—(Ra)—C(O)N—RaRb, S—Ra, —S(O)—Ra, —S(O)$_2$—Ra, S(O)$_2$—RaRb, wherein Ra and Rb are independently selected from the group consisting of hydrogen, alkyl, haloalkyl, aryl and arylalkyl; $R_3$ is selected from the group consisting of alkyl and haloalkyl; $R_4$ is alkyl, and $R_5$ is selected from the group consisting of halogen, aryl, and heteroaryl, wherein aryl, and heteroaryl can be independently substituted with 0, 1, 2, 3 or 4 substituents independently selected from alkenyl, alkyl, alkynyl, cyano, halo, haloalkyl, nitro, ethylenedioxy, methylenedioxy, —C(O)NRaRb, —C(O)ORa, —C(O)Ra, —NRaRb, alkylNRaRb, —ORa, —OC(O)Ra, alkylORa, —N(Ra)C(O)ORb, —N(Ra)C(O)NRaRb, SRa, —S(O)Ra, —S(O)$_2$Ra, S(O)$_2$RaRb, wherein Ra and Rb are independently selected from the group consisting of hydrogen, alkyl, haloalkyl, aryl and arylalkyl; and $R_6$ and $R_7$ are independently selected from the group consisting of hydrogen and alkyl.

In another embodiment, the present invention relates to compounds of formula (I), in which $R_1$ is alkyl, and in which both $R_2$ and $R_5$ are aryl.

In another embodiment, the present invention relates to compounds of formula (I) in which $R_2$ is phenyl and $R_5$ can be naphthyl, phenyl, 1,3-benzodioxolyl and 2,3-dihydro-1,4-benzodioxinyl. In a preferred embodiment $R_2$ is phenyl substituted with 0, 1, 2, or 3 alkyl, halo or haloalkyl group. In a preferred embodiment, $R_5$ is phenyl, which can be independently substituted with 0, 1, 2, or 3, halo, —ORa, methylenedioxy, ethylenedioxy, cyano, and —SRa group. In another preferred embodiment, $R_5$ is naphthyl. In yet another preferred embodiment $R_5$ is 1,3-benzodioxolyl or 2,3-dihydro-1,4-benzodioxinyl.

Another embodiment of the present invention relates to a compound of formula (I) in which $R_1$ is a bond, $R_2$ is phenyl substituted with 0, 1, 2, or 3 substituents selected from the group consisting of alkyl, halo, and haloalkyl kyl. $R_5$ can be naphthyl or phenyl. In a preferred embodiment, $R_5$ is phenyl, which can be independently substituted with 0, 1, 2, 3, or 4 alkyl, halo, —ORa, —SRa, and cyano groups.

In yet another embodiment, the present invention relates to a compound of formula (I) in which $R_1$ is alkyl, $R_2$ is aryl and $R_5$ is heteroaryl. In a preferred embodiment, $R_2$ is phenyl substituted with 0, 1, 2, or 3 substituents selected from the group consisting of alkyl, halo, and haloalkyl and $R_5$ is selected from the group of quinolinyl, thienyl and pyridinyl.

In yet another embodiment, the present invention discloses a compound of formula (I) in which $R_1$ is alkyl, $R_2$ is aryl, in which aryl is phenyl substituted with 0, 1, 2, or 3 substituents selected from the group consisting of alkyl, halo, and haloalkyl, $R_4$ is alkyl and, $R_5$ is halogen.

In yet another embodiment, the present invention discloses a compound of formula (I) in which $R_2$ is heteroaryl, wherein heteroaryl can be selected form the group of pyridinyl and quinolinyl, and $R_5$ is aryl. In a preferred embodiment, $R_1$ is alkyl, $R_2$ is pyridinyl and $R_5$ is aryl. In a most preferred embodiment, $R_2$ is pyridinyl substituted with 0, 1, 2, or 3 substituents independently selected from the group comprising alkyl, halo, and haloalkyl, and $R_5$ is phenyl, which can be independently substituted with 0, 1, 2, 3, or 4 alkoxy and halogen group.

Another embodiment of the present invention discloses a compound of formula (I) in which $R_2$ and $R_5$ are both heteroaryl groups. In a preferred embodiment, $R_1$ is alkyl, $R_2$ is pyridinyl and $R_5$ is quinolinyl. In a most preferred embodiment, $R_2$ is pyridinyl substituted with alkyl group.

In another preferred embodiment, the present invention discloses a compound in which $R_1$ is alkyl, $R_2$ is quinolinyl and $R_5$ is phenyl, most preferably a phenyl substituted with 0, 1, 2, 3, or 4 halogen group.

Another embodiment of the present invention relates to a compound of formula (I) in which $R_1$ is a bond, $R_2$ is quinolinyl and $R_5$ is phenyl. In a most preferred embodiment, $R_5$ is phenyl substituted with 0, 1, 2, 3, or 4 alkoxy and halogen group.

In yet another embodiment, the present invention relates to a compound of formula (II)

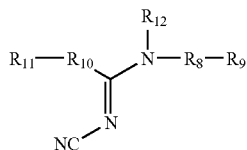

or a pharmaceutically acceptable salt or prodrug thereof, wherein $R_{10}$ is a carbon chain selected from the group consisting of alkyl, alkenyl, and alkynyl, $R_{11}$ is selected from the group consisting of aryl and heteroaryl, wherein aryl and heteroaryl are independently substituted with 0, 1, 2, 3 or 4 substituents independently selected from alkenyl, alkyl, alkynyl, halo, haloalkyl, nitro, —C(O)—N—RaRb, —C(O)O—Ra, —C(O)—Ra, —N—RaRb, alkyl-N—RaRb, —O—Ra, —OC(O)—Ra, alkyl-O—Ra, —N—(Ra)—C(O)O—Rb, —N—(Ra)—C(O)N—RaRb, S—Ra, —S(O)—Ra, —S(O)$_2$—Ra, S(O)$_2$—RaRb, wherein Ra and Rb are independently selected form the group consisting of hydrogen, alkyl, haloalkyl, aryl and arylalkyl; $R_8$ is a bond or a carbon chain selected from the group consisting of alkyl, alkenyl, and alkynyl, wherein the carbon chain selected from the group consisting of alkyl, alkenyl, and alkynyl, wherein the carbon chain can be substituted with 0, 1, or 2 substituents selected from the group consisting of —NH$_2$, —N(H)alkyl, —N(alkyl)$_2$, and heterocycle; $R_9$ is selected from the group consisting of aryl and heteroaryl, wherein aryl and heteroaryl are independently substituted with 0, 1, 2, 3 or 4 substituents independently selected from alkenyl, alkyl, alkynyl, cyano, halo, haloalkyl, nitro, heterocycle, —C(O)NRaRb, —C(O)ORa, —C(O)Ra, —NRaRb, alkylNRaRb, —ORa, —OC(O)Ra, alkylORa, —N(Ra)C(O)ORb, —N(Ra)C(O)NRaRb, SRa, —S(O)Ra, —S(O)$_2$Ra, S(O)$_2$RaRb, wherein Ra and Rb are independently selected form the group consisting of hydrogen, alkyl, haloalkyl, aryl and arylalkyl; and $R_{12}$ is selected from the group consisting of hydrogen and alkyl; in an alternative embodiment, $R_{12}$ and $R_8$ together with the nitrogen to which they are attached form a 4, 5, or 6 membered heterocycle ring, or when $R_9$ is aryl, $R_{12}$ along with any available carbon atom of $R_9$ form a 5 or 6 membered heterocycle ring, with the proviso that when $R_{11}$ is unsubstituted aryl or aryl substituted with 0, 1, 2, 3 or 4 halogen, and $R_{12}$ is selected from the group consisting hydrogen and alkyl, then $R_9$ is not substituted pyridinyl.

In another embodiment of the present invention, a compound of formula (II) is disclosed in which $R_{10}$ is alkyl, $R_{11}$ is aryl, and $R_8$ is selected from the group consisting of a bond and a carbon chain. In a preferred embodiment $R_{10}$ is phenyl substituted with 0, 1, 2, 3, or 4 substituents independently selected from the group consisting of halo, alkyl, and haloalkyl. In another preferred embodiment, $R_8$ is a bond, and $R_9$ is aryl. In yet another embodiment, $R_8$ is a carbon chain selected from the group consisting of alkyl, alkenyl, and alkynyl, wherein the carbon chain can be substituted with 0, 1, or 2 —NH$_2$, —N(H)alkyl, —N(alkyl)$_2$, or heterocycle, and $R_9$ is aryl.

In yet another embodiment, the present invention relates to a compound of formula (II) in which $R_8$ is a carbon chain selected from the group consisting of alkyl, alkenyl, and alkynyl, wherein the carbon chain can be substituted with 0, 1, or 2 —NH$_2$, —N(H)alkyl, —N(alkyl)$_2$, or morpholinyl; $R_9$ is phenyl substituted with 0, 1, 2, 3, or 4, substituents independently selected form the group of alkyl, halo and haloalkyl, and, $R_{11}$ is phenyl substituted with 0, 1, 2, 3, or 4, substituents independently selected form the group of alkyl, halo and haloalkyl.

In yet another embodiment, the present invention relates to a compound of formula (II) in which $R_9$ is heteroaryl and $R_{11}$ is aryl. Most preferably, $R_9$ is selected from the group of thienyl and pyridinyl.

In another embodiment, the present invention relates to a compound of formula (II), wherein $R_8$ is a bond, $R_9$ is aryl and $R_{11}$ is aryl. Most preferably, $R_9$ is selected from the group of 2,3-dihudro-indenyl, 1,2,3,4-tetrahydronaphthalenyl and 1,2,3,4-tetrahydro-1,4-methanopahthalenyl each independently substituted with 1, 2, 3, or 4 halogen, alkyl, and alkoxy groups.

In another embodiment, the present invention relates to a compound of formula (II), wherein 1,2,3,4-tetrahydronaphthalenyl can be substituted with 0, 1 or 2 substituents selected from the group consisting of alkyl and alkoxy.

In another embodiment, the present invention relates to a compound of formula (II) in which $R_{11}$ is heteroaryl, and $R_9$ is aryl. In a preferred embodiment, $R_{11}$ is pyridinyl and $R_9$ is phenyl In a most preferred embodiment, $R_{11}$ is pyridinyl substituted with alkyl, and $R_9$ is phenyl substituted with 0, 1, 2, 3, or 4 halogen, alkyl and alkoxy groups.

In yet another embodiment of the present invention relates to a compound of formula (II) in which $R_8$ is alkyl, $R_{11}$ is quinolinyl and $R_9$ is preferably selected from the group of 2,3-dihydro-indenyl and 1,2,3,4-tetrahydronaphthalenyl, In another embodiment, the present invention relates to a method of treating a disorder selected from the group consisting of pain, rheumatoid arthritis, osteoarthritis, psoriasis, allergic dermatitis, asthma, chronic obstructive pulmonary disease, airways hyper-responsiveness, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischemic heart disease, stroke and varicose veins in a mammal comprising administering to the mammal a therapeutically effective amount of a compound of formula (I) or a pharmaceutically acceptable salt or prodrug thereof. In a most preferred embodiment, the present invention relates to a method of treating pain in a mammal comprising administering to the mammal a therapeutically effective amount of a compound of formula (I) or a pharmaceutically acceptable salt or prodrug thereof.

In yet another embodiment, the present invention relates to a method of treating a disorder selected from the group consisting of pain, rheumatoid arthritis, osteoarthritis, psoriasis, allergic dermatitis, asthma, chronic obstructive pulmonary disease, airways hyper-responsiveness, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischemic heart disease, stroke and varicose veins in a mammal comprising administering to the mammal a therapeutically effective amount of a compound of formula (II) or a pharmaceutically acceptable salt or prodrug thereof.

In yet another embodiment, the present invention relates to a method of treating pain in a mammal comprising administering to the mammal a therapeutically effective amount of a compound of formula (II) or a pharmaceutically acceptable salt or prodrug thereof.

(c) Methods for Preparing Compounds of the Invention

The compounds and processes of the present invention will be better understood in connection with the following synthetic schemes and methods, which illustrate a means by which the compounds of the invention can be prepared.

The compounds of this invention may be prepared by a variety of synthetic routes. Representative procedures are shown in Schemes 1-3.

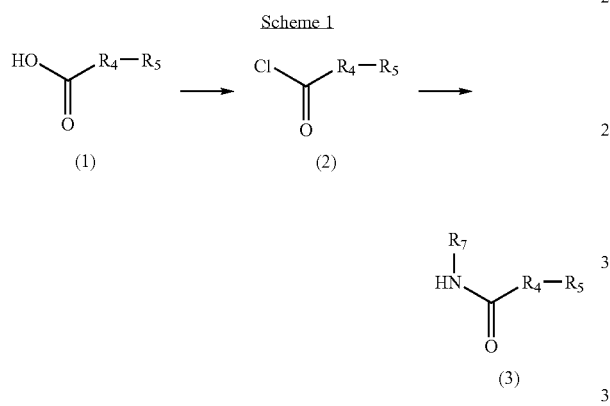

Compounds of formula (3) can be prepared from the corresponding carboxylic acids. Typically by reaction of compounds of formula (1) with (a) thionyl chloride or oxalyl chloride, optionally in the presence of dimethylformamide, at a temperature from about 0° C. to about 60° C., in a solvent such as, but is not limited to, dichloromethane, tetrahydrofuran, chloroform or dioxane, for a period of about 1 hour to about 24 hours, and (b) reacting product from step (a) with an amine having formula $R_7NH_2$ in a solvent such as, but not limited to, tetrahydrofuran, dichloromethane, methanol, dioxane or water, at a temperature from about 0° C. to about 25° C., for a period of about 30 minutes to about 3 hours.

Alternatively, compounds of formula (3) can be prepared from an ester having formula $R_5$—$R_4$—$C(O)OR_{100}$, wherein $R_{100}$ is alkyl or aryl, preferably p-nitrophenyl, by reaction with ammonia in a solvent such as, but is not limited to, methanol or ethanol, at a temperature from about 20° C. to about 80° C., for a period of about 2 hours to about 120 hours. The reaction is usually performed in a sealed container.

Alternatively, compounds of formula (3) can be prepared from compounds of formula (1), by reaction with an amine of formula $R_7NH_2$, in the presence of a coupling reagent, such as 1-[3-(dimethylamino)propyl]-3-ethylcarbodiimide (EDC) or dicyclohexyl carbodiimide (DCC) and hydroxybenzotriazole hydrate (HOBT), and a base, such as diisopropylethylamine or triethylamine, in an aprotic solvent, such as but not limited to, dichloromethane. The reaction can be run at a temperature from about 0° C. to about 50° C., for a period of about 1 hour to about 24 hours.

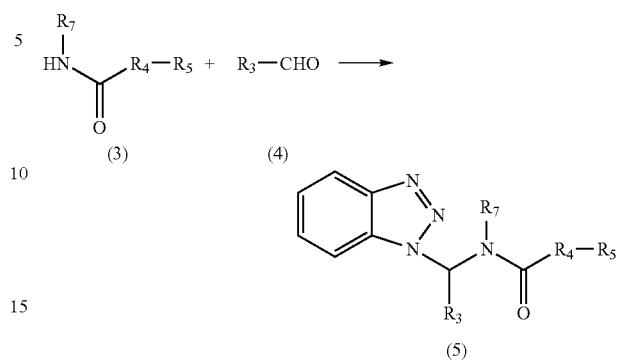

Compounds of formula (5) can be prepared from compounds of formula (3) by reaction with aldehydes of formula (4) and 1H-1,2,3-benzotriazole in the presence of an acid such as, but not limited to p-toluenesulfonic acid, pyridium p-toluensulfonate, benzenesulfonic acid or camphorsulfonic acid in an organic solvent such as, but not limited to, toluene, benzene or xylene. The aforesaid reaction can be performed at about reflux temperature of the solvent employed and preferably using Dean-Stark apparatus to aid the removal of water.

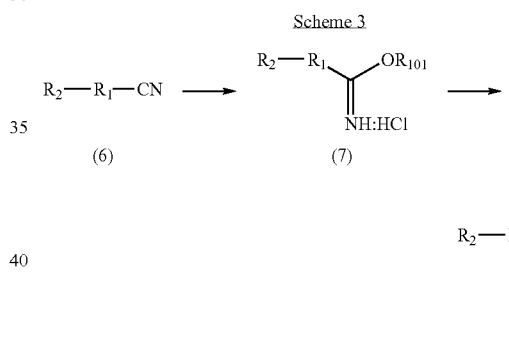

Compounds of formula (6) can be converted to salts of imino esters having formula (7) by reaction with dry hydrogen chloride and an alcohol having formula $R_{101}OH$, wherein $R_{101}$ is alkyl and preferably ethyl, in the absence of water. The reaction can be performed neat or in the presence of an organic solvent such as dichloromethane, at a temperature from about 0° C. to about 25° C. for a period of about 12 hours to about 72 hours.

Compounds of formula (7) can be converted to compounds of formula (8) by reaction with cyanamides of formula $NH_2CN$, in the presence of a base such as metal alkoxide having formula $MOR_{101}$ (for example sodium ethoxide, sodium methoxide, potassium t-butoxide, and the like) wherein M is a monovalent metal, in a solvent such as methanol or ethanol. The reaction can be run at a temperature from about 20° C. to about 60° C. for a period of about 1 hour to about 24 hours.

Alternatively compounds of formula (8) can be prepared from compounds of formula (6) directly by reaction with sodium cyanamide in an alcoholic solvent having formula $R_{101}OH$ (for example ethanol) at reflux temperature for about 1 hour to about 24 hours.

Scheme 4

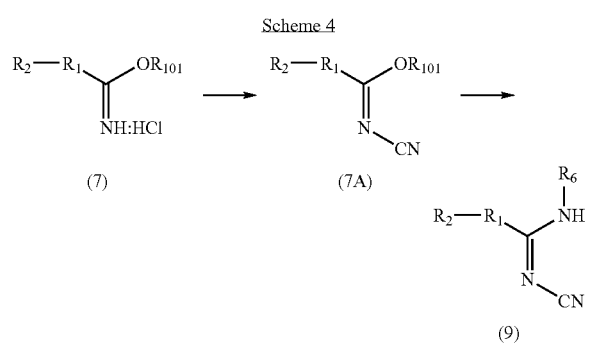

Compounds of formula (7A) can be prepared from compounds of formula (7) by reaction with cyanamide and an alcohol having formula $R_{101}OH$ in a solvent such as, but not limited to, dichloromethane or diethyl ether, at a temperature from about 25° C. to about 80° C. for a period of about 1 hour to about 24 hours. Compound of formula (7A) can be reacted with amines of formula $R_6NH_2$ in an alcoholic solvent of formula $R_{101}OH$ at a temperature from about 50° C. to about 100° C. for a period of about 1 hour to about 24 hours, to afford compounds of formula (9).

Scheme 5

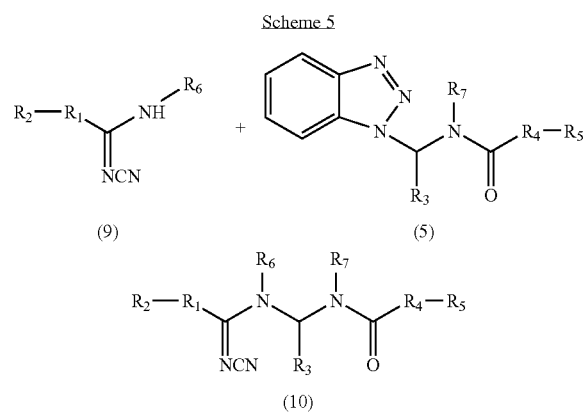

Compounds of formula (10) can be prepared from compounds of formula (9) by reaction with compounds of formula (5) in the presence of an anhydrous base at a temperature from about 25° C. to about 60° C. for a period of about 5 hours to about 24 hours. The reaction can be run in a solvent such as, but not limited to dichloromethane, acetonitrile, toluene, N,N,dimethyl formamide (DMF), dioxane, ethyl acetate or dimethylsulfoxide. Examples of the anhydrous base include, but not limited to, metal carbonates such as cesium carbonate, potassium carbonate, organic amines such as imidazole, 1-methyl imidazole, piperidine, pyrrolidine, triethylamine, diisopropylethyl amine, and metal hydroxides such as lithium hydroxide.

Scheme 6

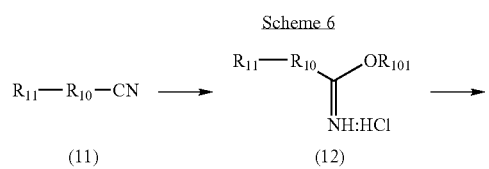

Compounds of formula (12) wherein $R_{101}$ is alkyl, can be prepared from nitriles of formula (11) using the conditions for the transformation of compounds of formula (6) to compounds of formula (7) as described in Scheme 3.

Compounds of formula (13) can be prepared from compounds of formula (12) by reaction with cyanamide and an alcohol having formula $R_{101}OH$ in a solvent such as, but not limited to, dichloromethane or diethyl ether, at a temperature from about 25° C. to about 80° C. for a period of about 1 hour to about 24 hours.

Scheme 7

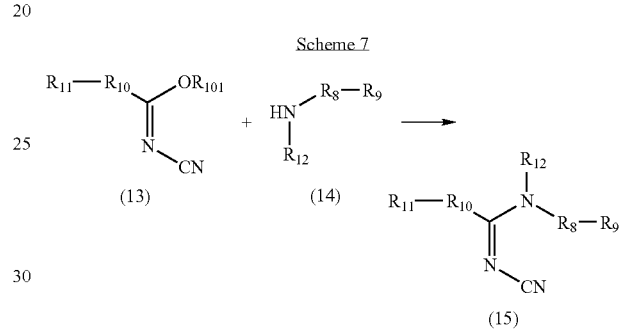

Compound of formula (13) can be reacted with amines of formula (14) in an alcoholic solvent of formula $R_{101}OH$ at a temperature from about 50° C. to about 100° C. for a period of about 1 hour to about 24 hours, to afford compounds of formula (15).

(d) Compositions of the Invention

The present invention provides pharmaceutical compositions, which comprise compounds of the present invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration that include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin. In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions that can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin); f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

The terms "pharmaceutically acceptable salts, esters and amides," as used herein, refer to carboxylate salts, amino acid addition salts, zwitterions, esters and amides of compounds of formula I which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt," as used herein, refers to salts that are well known in the art. For example, S. M Berge et al. describe pharmaceutically acceptable salts in detail in *J. Pharmaceutical Sciences, Vol.* 66, pages 1-19 (1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I may be prepared according to conventional methods. It is intended that amides of the present invention include amino acid and peptide derivatives of the compounds of formula I, as well.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, "Pro-drugs as Novel Delivery Systems" V. 14 of the A.C.S. Symposium Series, and in Edward B. Roche, ed., "Bioreversible Carriers in Drug Design", American Pharmaceutical Association and Pergamon Press (1987), hereby incorporated by reference.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 50 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

(e) EXAMPLES OF THE PRESENT INVENTION

Example 1

N-(1-{[N-cyano-2-(2-methylphenyl)ethanimidoyl]amino}-2,2-dimethylpropyl)-2-phenylacetamide Example 1A N-[1-(1H-1,2,3-benzotriazol-1-yl)-2,2-dimethylpropyl]-2-phenylacetamide A suspension of phenylacetamide (2.9 g, 21.45 mmol), trimethylacetaldehyde (5.42 g, 63.00 mmol), and 1H-1,2,3-benzotriazole (2.56 g, 21.45 mmol) in toluene (75 mL) was treated with p-toluenesulfonic acid (0.200 g, 1.00 mmol). The solution was heated at reflux under Dean-Stark conditions for 10 hours, cooled gradually to ambient temperature. The mixture was concentrated under reduced pressure and purified by flash chromatography on silica gel (sequential elution with 10, 15, and 20% of ethyl acetate in methylene chloride) to provide 6.05 g of the title compound. MS (ESI$^+$) m/z 323 (M+H)$^+$.

Example 1B ethyl 2-(2-methylphenyl)ethanimidoate hydrochloride

The title compound was prepared using the procedure as described in Ife, R. J. et al. (WO 9315055).

Example 1C

N'-cyano-2-(2-methylphenyl)ethanimidamide

A solution of Example 1B (4 g, 18.72 mmol)) in absolute ethanol (50 ml) was treated with a 21% sodium ethoxide solution in ethanol (7 ml, 18.72 mmol) and the precipitated sodium chloride was filtered off. The filtrate was then treated with a solution of cyanamide (0.79 g, 18.72 mmol) in absolute ethanol (25 ml) and stirred at room temperature for one hour. The solvent was evaporated under reduced pressure. The residual oil was triturated with ether to afford white crystals that were filtered and dried to yield 2.5 g of product. MS (ESI$^+$) m/z 174 (M+H)$^+$.

Example 1D

N-(1-{[N-cyano-2-(2-methylphenyl)ethanimidoyl]amino}-2,2-dimethylpropyl)-2-phenylacetamide A solution of Example 1A (104 mg, 0.6 mmol) and Example 1C (194 mg, 0.6 mmol) in CH$_3$CN (4 mL) at about 23° C. was treated with finely powdered anhydrous Cs$_2$CO$_3$ (529 mg, 1.5 mmol). The reaction mixture was stirred for 10 hours. The suspension was filtered through a pad of Celite and washed with ethyl acetate. The filtrate was concentrated under reduced pressure and purified by preparative HPLC on a Waters Symmetry C8 column (40 mm×100 mm, 7 μm particle size) using a gradient of 10% to 100% of acetonitrile in a 10 mM aqueous solution of ammonium acetate over 15 min at a flow rate of 70 mL/min to provided 136 mg of the title compound. mp 182-183° C.; MS (ESI$^+$) m/z 377 (M+H)$^+$; $^1$H NMR (400 MHz, DMSO-d$_6$) δ ppm 0.92 (s, 9H) 2.26 (s, 3H) 3.53 (m, 2H) 3.84 (s, 2H) 5.64 (t, J=8.59 Hz, 1H) 7.04 (m, 2H) 7.23 (m, 7H) 8.15 (d, J=8.59 Hz, 1H) 8.67 (d, J=8.59 Hz, 1H); anal. calcd for C$_{23}$H$_{28}$N$_4$O: C, 73.37; H, 7.50; N, 14.88. Found: C, 73.00; H, 7.70; N, 14.81.

Example 2

2-(4-chlorophenyl)-N-(1-{[N-cyano-2-(2-methylphenyl)ethanimidoyl]amino}-2,2-dimethylpropyl)acetamide Example 2A 2-(4-chlorophenyl)acetamide The title compound was prepared using the procedure as described in Freudenreich, C et al., *J. Amer. Chem. Soc., Vol.* 106, pages 3344-3553 (1984).

Example 2B

N-[1-(1H-1,2,3-benzotriazol-1-yl)-2,2-dimethylpropyl]-2-(4-chlorophenyl)acetamide The title compound was prepared using the procedure as described in Example 1A, substituting 2-(4-chlorophenyl)acetamide for phenylacetamide. MS (ESI$^+$) m/z 357 (M+H)$^+$.

Example 2C 2-(4-chlorophenyl)-N-(1-{[N-cyano-2-(2-methylphenyl)ethanimidoyl]amino}-2,2-dimethylpropyl)acetamide The title compound was prepared according to the procedure as described in Example 1D, substituting Example 2B for Example 1A. mp 183-185° C.; MS (ESI$^+$) m/z 411 (M+H)$^+$; $^1$H NMR (300 MHz, DMSO-d$_6$) δ ppm 0.92 (s, 9H) 2.26 (s, 3H) 3.53 (s, 2H) 3.83 (s, 2H) 5.62 (t, J=8.65 Hz, 1H) 7.01 (m, 2H) 7.18 (m, 2H) 7.31 (m, 4H) 8.18 (d, J=8.48 Hz, 1H) 8.66 (d, J=8.48 Hz, 1H). Anal. calcd for C$_{23}$H$_{27}$ClN$_4$O: C, 67.22; H, 6.62; N, 13.63. Found: C, 66.87; H, 6.32; N, 13.51.

Example 3

N-(1-{[N-cyano-2-(2-methylphenyl)ethanimidoyl]amino}-2,2-dimethylpropyl)-2-(3,4-dimethoxyphenyl)acetamide

Example 3A

N-[1-(1H-1,2,3-benzotriazol-1-yl)-2,2-dimethylpropyl]-2-(3,4-dimethoxyphenyl)acetamide The title compound was prepared using the procedure as described in Example 1A, substituting 2-(3,4-dimethoxyphenyl)acetamide for phenylacetamide. MS (ESI$^+$) m/z 383 (M+H)$^+$.

Example 3B

N-(1-{[N-cyano-2-(2-methylphenyl)ethanimidoyl]amino}-2,2-dimethylpropyl)-2-(3,4-dimethoxyphenyl)acetamide The title compound was prepared with the procedure as described in Example 1D substituting Example 3A for Example 1A. mp 153-155° C.; MS (ESI$^+$) m/z 437 (M+H)$^+$; $^1$H NMR (300 MHz, DMSO-d$_6$) δ ppm 0.92 (s, 9H) 2.27 (s, 3H) 3.44 (m, 2H) 3.71 (d, J=4.75 Hz, 6H) 3.84 (s, 2H) 5.64 (t, J=8.65 Hz, 1H) 6.77 (dd, J=8.31, 1.86 Hz, 1H) 6.86 (m, 2H) 7.05 (m, 2H) 7.19 (m, 2H) 8.05 (d, J=8.48 Hz, 1H) 8.63 (d, J=8.48 Hz, 1H). Anal. calcd for C$_{25}$H$_{32}$N$_4$O$_3$: C, 68.78; H, 7.39; N, 12.83. Found: C, 68.55; H, 7.12; N, 12.75.

Example 4

N-(1-{[N-cyano-2-(2-methylphenyl)ethanimidoyl]amino}-2,2-dimethylpropyl)-2-(4-methoxyphenyl)acetamide

Example 4A

N-[1-(1H-1,2,3-benzotriazol-1-yl)-2,2-dimethylpropyl]-2-(4-methoxyphenyl)acetamide The title compound was prepared using the procedure as described in Example 1A, substituting 2-(4-methoxyphenyl)acetamide for phenylacetamide. MS (ESI$^+$) m/z 353 (M+H)$^+$;

Example 4B

N-(1-{[N-cyano-2-(2-methylphenyl)ethanimidoyl]amino}-2,2-dimethylpropyl)-2-(4-methoxyphenyl)acetamide The title compound was prepared using the procedure as described in Example 1D, substituting Example 4A for Example 1A. mp 199-201° C.; MS (ESI$^+$) m/z 407 (M+H)$^+$; $^1$H NMR (300 MHz, DMSO-d$_6$) δ ppm 0.91 (s, 9H) 2.26 (s, 3H) 3.44 (m, 2H) 3.72 (s, 3H) 3.83 (s, 2H) 5.63 (t, J=8.65 Hz, 1H) 6.85 (m, 2H) 7.04 (m, 2H) 7.18 (m, 4H) 8.07 (d, J=8.81 Hz, 1H) 8.66 (d, J=8.48 Hz, 1H). Anal. calcd for C$_{24}$H$_{30}$N$_4$O$_2$: C, 70.91; H, 7.44; N, 13.78. Found: C, 70.56; H, 7.76; N, 13.81.

Example 5

2-(1,3-benzodioxol-5-yl)-N-(1-{[N-cyano-2-(2-methylphenyl)ethanimidoyl]amino}-2,2-dimethylpropyl)acetamide

Example 5A 2-(1,3-benzodioxol-5-yl)acetamide

The title compound was prepared using the procedure as described in Mastagli et al; *Bull. Soc. Chim. Fr.*, pages 662-665 (1948).

Example 5B 2-(1,3-benzodioxol-5-yl)-N-[1-(1H-1,2,3-benzotriazol-1-yl)-2,2-dimethylpropyl]acetamide The title compound was prepared using the procedure as described in Example 1A, substituting Example 5A for phenylacetamide. MS (ESI$^+$) m/z 367(M+H)$^+$;

Example 5C 2-(1,3-benzodioxol-5-yl)-N-(1-{[N-cyano-2-(2-methylphenyl)ethanimidoyl]amino}-2,2-dimethylpropyl)acetamide The title compound was prepared using the procedure as described in Example 1D, substituting Example 5B for Example 1A. mp 167-169° C.; MS (ESI$^+$) m/z 421 (M+H)$^+$; $^1$H NMR (300 MHz, DMSO-d$_6$) δ ppm 0.91 (s, 9H) 2.26 (s, 3H) 3.42 (m, 2H) 3.82 (m, 2H) 5.63 (t, J=8.48 Hz, 1H) 5.97 (s, 2H) 6.71 (dd, J=7.80, 1.70 Hz, 1H) 6.81 (m, 2H) 7.03 (m, 2H) 7.18 (m, 2H) 8.12 (d, J=8.48 Hz, 1H) 8.71 (d, J=8.14 Hz, 1H). Anal. calcd for C$_{24}$H$_{28}$N$_4$O$_3$0.25 CH$_3$OH: C, 67.97; H, 6.82; N, 13.07. Found: C, 68.03; H, 7.22; N, 13.27.

Example 6

N-(1-{[N-cyano-2-(2-methylphenyl)ethanimidoyl]amino}-2,2-dimethylpropyl)-2-(4-cyanophenyl)acetamide

Example 6A 2-(4-cyanophenyl)acetamide

The title compound was prepared using the procedure as described in Mellinghoff, *Chem. Ber., Vol.* 22, page 3208 (1889).

Example 6B

N-[1-(1H-1,2,3-benzotriazol-1-yl)-2,2-dimethylpropyl]-2-(4-cyanophenyl)acetamide The title compound was prepared using the procedure as described in Example 1A, substituting Example 6A for phenylacetamide. MS (ESI$^+$) m/z 348 (M+H)$^+$.

Example 6C

N-(1-[N-cyano-2-(2-methylphenyl)ethanimidoyl]amino-2,2-dimethylpropyl)-2-(4-cyanophenyl)acetamide The title compound was prepared using the procedure as described in Example 1D, substituting Example 6C for Example 1A. mp 199-201° C.; MS (ESI$^+$) m/z 402 (M+H)$^+$; $^1$H NMR (400 MHz, DMSO-d$_6$) δ ppm 0.93 (s, 9H) 2.26 (s, 3H) 3.65 (s, 2H) 3.83 (s, 2H) 5.61 (t, J=8.59 Hz, 1H) 7.01 (m, 2H) 7.18 (m, 2H) 7.46 (d, J=8.29 Hz, 2H) 7.75 (dt, J=8.29, 1.84 Hz, 2H) 8.28 (d, J=8.59 Hz, 1H) 8.69 (d, J=8.28 Hz, 1H) Anal. calcd for C$_{24}$H$_{27}$N$_5$O0.05H$_2$O: C, 71.63; H, 6.79; N, 17.40. Found: C, 71.26; H, 6.77; N, 17.28.

Example 7

N-(1-{[N-cyano-2-(2-methylphenyl)ethanimidoyl]amino}-2,2-dimethylpropyl)-2-(2,3-dihydro-1,4-benzodioxin-6-yl)acetamide

Example 7A

2,3-Dihydro-1,4-benzodioxin-6-ylacetic acid

The title compound was prepared using the procedure as described in Vazquez, et al., *Farmaco* Vol. 51 pages 215-218 (1996).

Example 7B

2-(2,3-dihydro-1,4-benzodioxin-6-yl)acetamide

The title compound was prepared using the procedure as described in Example 13A, substituting Example 7A for 2-(3,4-difluorophenyl)acetic acid. MS (ESI$^+$) m/z 211 (M+NH$_3$)$^+$.

Example 7C

N-[1-(1H-1,2,3-benzotriazol-1-yl)-2,2-dimethylpropyl]-2-(2,3-dihydro-1,4-benzodioxin-6-yl)acetamide The title compound was prepared using the procedure as described in Example 1A, substituting Example 7B for phenylacetamide. MS (ESI$^+$) m/z 381 (M+H)$^+$;

Example 7D

N-(1-{[N-cyano-2-(2-methylphenyl)ethanimidoyl]amino}-2,2-dimethylpropyl)-2-(2,3-dihydro-1,4-benzodioxin-6-yl)acetamide The title compound was prepared according to the procedure of Example 1D, substituting Example 7C for Example 1A. mp 180-181° C.; MS (ESI$^+$) m/z 435 (M+H)$^+$; $^1$H NMR (400 MHz, DMSO-d$_6$) δ ppm 0.91 (s, 9H) 2.26 (s, 3H) 3.39 (m, 2H) 3.83 (s, 2H) 4.20 (s, 4H) 5.63 (t, J=8.59 Hz, 1H) 6.70 (dd, J=8.29, 1.84 Hz, 1H) 6.76 (m, 2H) 7.04 (m, 2H) 7.18 (m, 2H) 8.08 (d, J=8.59 Hz, 1H) 8.68 (d, J=8.90 Hz, 1H). Anal. calcd for C$_{25}$H$_{30}$N$_4$O$_3$0.075H$_2$O: C, 68.89; H, 6.97; N, 12.85. Found: C, 68.49; H, 7.23; N, 12.80.

Example 8

N-(1-{[N-cyano-2-(2-methylphenyl)ethanimidoyl]amino}-2,2-dimethylpropyl)-2-fluoroacetamide

Example 8A

N-[1-(1H-1,2,3-benzotriazol-1-yl)-2,2-dimethylpropyl]-2-fluoroacetamide

The title compound was prepared using the procedure as described in Example 1A, substituting 2-fluoroacetamide for phenylacetamide. MS (ESI$^+$) m/z 265 (M+H)$^+$.

Example 8B

N-(1-{[N-cyano-2-(2-methylphenyl)ethanimidoyl]amino}-2,2-dimethylpropyl)-2-fluoroacetamide The title compound was prepared using the procedure of Example 1D, substituting Example 8A for Example 1A. mp 151-152° C.; MS (ESI$^+$) m/z 319 (M+H)$^+$; $^1$H NMR (400 MHz, DMSO-d$_6$) δ ppm 0.89 (s, 9H) 2.29 (s, 3H) 3.89 (m, 2H) 4.81 (m, 1H) 4.92 (m, 1H) 5.73 (t, J=8.75 Hz, 1H) 7.10 (m, 1H) 7.20 (m, 3H) 8.14 (d, J=8.90 Hz, 1H) 8.45 (d, J=8.28 Hz, 1H). Anal. calcd for C$_{17}$H$_{23}$FN$_4$O: C, 64.13; H, 7.28; N, 17.60. Found: C, 63.93; H, 7.49; N, 17.65.

Example 9

N-(1-{[N-cyano-2-(2-methylphenyl)ethanimidoyl]amino}-2,2-dimethylpropyl)-2-(1-naphthyl)acetamide

Example 9A

N-[1-(1H-1,2,3-benzotriazol-1-yl)-2,2-dimethylpropyl]-2-(1-naphthyl)acetamide The title compound was prepared using the procedure of Example 1A, substituting 2-(1-naphthyl)acetamide for phenylacetamide. MS (ESI$^+$) m/z 373 (M+H)$^+$.

Example 9B

N-(1-{[N-cyano-2-(2-methylphenyl)ethanimidoyl]amino}-2,2-dimethylpropyl)-2-(1-naphthyl)acetamide The title compound was prepared using the procedure of Example 1D, substituting Example 9A for Example 1A. mp 97-100° C.; MS (ESI$^+$) m/z 427 (M+H)$^+$; $^1$H NMR (400 MHz, DMSO-d$_6$) δ ppm 0.94 (s, 9H) 2.27 (s, 3H) 3.84 (s, 2H) 4.01 (m, 2H) 5.66 (t, J=8.59 Hz, 1H) 7.00 (m, 2H) 7.17 (m, 2H) 7.43 (m, 2H) 7.52 (m, 2H) 7.83 (m, 1H) 7.92 (m, 1H) 8.07 (m, 1H) 8.27 (d, J=8.29 Hz, 1H) 8.68 (d, J=8.29 Hz, 1H). Anal. calcd for C$_{27}$H$_{30}$N$_4$O: C, 76.03; H, 7.09; N, 13.13. Found: C, 75.73; H, 7.45; N, 13.04.

Example 10

N-(1-{[N-cyano-2-(2-methylphenyl)ethanimidoyl]amino}-2,2-dimethylpropyl)-2-quinolin-6-ylacetamide

Example 10A 2-(6-quinolinyl)acetamide

The title compound was prepared using the procedure as described in Tsatsaronis, K., *J. Org. Chem. Vol.* 35 page 438 (1970).

Example 10B

N-[1-(1H-1,2,3-benzotriazol-1-yl)-2,2-dimethylpropyl]-2-quinolin-6-ylacetamide

The title compound was prepared using the procedure as described in Example 1A, substituting Example 10A for phenylacetamide. MS (ESI$^+$) m/z 374 (M+H)$^+$;

Example 10C

N-(1-{[N-cyano-2-(2-methylphenyl)ethanimidoyl]amino}-2,2-dimethylpropyl)-2-quinolin-6-ylacetamide The title compound was prepared using the procedure as described in Example 1D, substituting Example 10B for Example 1A. mp 172-173° C.; MS (ESI$^+$) m/z 428 (M+H)$^+$; $^1$H NMR (400 MHz, DMSO-d$_6$) δ ppm 0.94 (s, 9H) 2.25 (s, 3H) 3.75 (s, 2H) 3.83 (s, 2H) 5.67 (t, J=8.44 Hz, 1H) 6.92 (t, J=6.90 Hz, 1H) 7.01 (m, 1H) 7.09 (td, J=7.29, 1.07 Hz, 1H) 7.17 (m, 1H) 7.50 (dd, J=8.29, 4.30 Hz, 1H) 7.68 (dd, J=8.59, 1.84 Hz, 1H) 7.81 (d, J=1.53 Hz, 1H) 7.95 (d, J=8.90 Hz, 1H) 8.27 (dd, J=8.29, 1.23 Hz, 1H) 8.37 (d, J=8.59 Hz, 1H) 8.81 (d, J=8.59 Hz, 1H) 8.86 (dd, J=4.30, 1.84 Hz, 1H). Anal. calcd for C$_{26}$H$_{29}$N$_5$O0.5H$_2$O: C, 71.53; H, 6.93; N, 16.04. Found: C, 71.27; H, 6.88; N, 15.96.

Example 11

N-(1-{[N-cyano-2-(2-methylphenyl)ethanimidoyl]amino}-2,2-dimethylpropyl)-2-quinolin-7-ylacetamide

Example 11A

7-Quinolinylacetic acid

The title compound was prepared using the procedure as described in Meyer, M. D. et al., *J. Med. Chem. Vol.* 40, pages 1049-1062 (1997).

Example 11B

Methyl 7-quinolinylacetate

To a solution of example 11A (1.98 g, 10.59 mmol) in 40 mL of anhydrous methanol was slowly added SOCl$_2$ (1.5 mL, 31.7 mmol), and a drop of dimethylformamide as catalyst. The mixture was refluxed for 5 hrs and then concentrated under reduced pressure. The residue was dissolved in water (10 mL) and neutralized with aqueous sodium bicarbonate to pH 8. The product was extracted with methylene chloride, dried with anhydrous sodium sulfate and concentrated under reduced pressure to afford 2.13 g of the title compound. MS (ESI$^+$) m/z 202 (M+H)$^+$.

Example 11C 2-(7-quinolinyl)acetamide

Example 11B (2.128 g, 10.59 mmol) was dissolved in 7N NH$_3$ solution in MeOH (15 mL) and stirred at 60° C. in a sealed tube for 48 hr. The solvent and excess ammonia were removed under reduced pressure to afford 1.026 g of the title compound. MS (ESI$^+$) m/z 187 (M+H)$^+$.

Example 11D

N-[1-(1H-1,2,3-benzotriazol-1-yl)-2,2-dimethylpropyl]-2-quinolin-7-ylacetamide

The title compound was prepared using the procedure as described in Example 1A, substituting Example 11C for phenylacetamide. MS (ESI$^+$) m/z 374 (M+H)$^+$.

Example 11E

N-(1-{[N-cyano-2-(2-methylphenyl)ethanimidoyl]amino}-2,2-dimethylpropyl)-2-quinolin-7-ylacetamide The title compound was prepared using the procedure as described in Example 1D, substituting Example 1D for Example 1A. mp 165-166° C.; MS (ESI$^+$) m/z 428 (M+H)$^+$; $^1$H NMR (400 MHz, DMSO-d$_6$) δ ppm 0.93 (s, 9H) 2.24 (s, 3H) 3.77 (m, 2H) 3.83 (s, 2H) 5.68 (t, J=8.59 Hz, 1H) 6.97 (m, 2H) 7.09 (td, J=7.21, 1.53 Hz, 1H) 7.16 (m, 1H) 7.49 (dd, J=8.13, 4.14 Hz, 1H) 7.54 (dd, J=8.44, 1.69 Hz, 1H) 7.91 (d, J=8.59 Hz, 2H) 8.34 (m, 2H) 8.78 (d, J=8.59 Hz, 1H) 8.88 (dd, J=4.14, 1.69 Hz, 1H). Anal. calcd for C$_{26}$H$_{29}$N$_5$O: C, 73.04; H, 6.84; N, 16.38. Found: C, 72.75; H, 6.88; N, 16.43.

Example 12

N-(1-{[N-cyano-2-(2-methylphenyl)ethanimidoyl]amino}-2,2-dimethylpropyl)-4-thien-2-ylbutanamide

Example 12A 4-(2-thienyl)butanamide

The title compound was prepared using the procedure as described in Blanchette et al., *J. Amer. Chem. Soc., Vol.* 74 page 1066 (1952).

Example 12B

N-[1-(1H-1,2,3-benzotriazol-1-yl)-2,2-dimethylpropyl]-4-thien-2-ylbutanamide

The title compound was prepared using the procedure as described in Example 1A, substituting Example 12A for phenylacetamide. MS (ESI$^+$) m/z 357 (M+H)$^+$;

Example 12C

N-(1-{[N-cyano-2-(2-methylphenyl)ethanimidoyl]amino}-2,2-dimethylpropyl)-4-thien-2-ylbutanamide The title compound was prepared using the procedure as described in Example 1D, substituting Example 12B for Example 1A. mp 154-155° C.; MS (ESI$^+$) m/z 411 (M+H)$^+$;

¹H NMR (400 MHz, DMSO-d$_6$) δ ppm 0.92 (s, 9H) 1.85 (m, 2H) 2.23 (td, J=7.29, 2.30 Hz, 2H) 2.28 (s, 3H) 2.79 (t, J=7.52 Hz, 2H) 3.84 (s, 2H) 5.65 (t, J=8.59 Hz, 1H) 6.82 (m, 1H) 6.94 (dd, J=5.22, 3.38 Hz, 1H) 7.14 (m, 4H) 7.31 (d, J=5.22, 1.23 Hz, 1H) 7.95 (d, J=8.59 Hz, 1H) 8.59 (d, J=8.29 Hz, 1H). Anal. calcd for C$_{23}$H$_{30}$N$_4$OS: C, 67.28; H, 7.36; N, 13.65. Found: C, 66.96; H, 7.70; N, 13.51.

Example 13

N-(1-{[N-cyano-2-(2-methylphenyl)ethanimidoyl]amino}-2,2-dimethylpropyl)-2-(3,4-difluorophenyl)acetamide

Example 13A 2-(3,4-difluorophenyl)acetamide

To a solution of 2-(3,4-difluorophenyl)acetic acid (5.1 g, 30.33 mmol) in 50 mL of anhydrous dichloromethane was added SOCl$_2$ (4.33 g, 36.4 mmol), and a drop of dimethylformamide as catalyst. The mixture was stirred at room temperature for 2 hr, solvent and excess SOCl$_2$ were removed under reduced pressure. The crude product was dissolved in 50 mL of THF, cooled to 0° C. and liquid ammonia was added dropwise through condenser for 20 minutes. The reaction mixture was concentrated, the product precipitated with 30 ml of water, filtered, and dried to afford 4.55 g of title compound. MS (ESI$^+$) m/z 172 (M+H)$^+$.

Example 13B

N-[1-(1H-1,2,3-benzotriazol-1-yl)-2,2-dimethylpropyl]-2-(3,4-difluorophenyl)acetamide The title compound was prepared using the procedure as described in Example 1A, substituting Example 13A for phenylacetamide. MS (ESI$^+$) m/z 359 (M+H)$^+$.

Example 13C

N-(1-{[N-cyano-2-(2-methylphenyl)ethanimidoyl]amino}-2,2-dimethylpropyl)-2-(3,4-difluorophenyl)acetamide The title compound was prepared using the procedure as described in Example 1D, substituting Example 13B for Example 1A. mp 178-179° C.; MS (ESI$^+$) m/z 413 (M+H)$^+$; ¹H NMR (400 MHz, DMSO-d$_6$) δ ppm 0.93 (s, 9H) 2.26 (s, 3H) 3.54 (s, 2H) 3.83 (s, 2H) 5.62 (t, J=8.59 Hz, 1H) 7.04 (m, 3H) 7.18 (m, 2H) 7.32 (m, 2H) 8.19 (d, J=8.28 Hz, 1H) 8.66 (d, J=8.29 Hz, 1H). Anal. calcd for C$_{23}$H$_{26}$F$_2$N$_4$O: C, 66.97; H, 6.35; N, 13.58. Found: C, 66.84; H, 6.60; N, 13.68.

Example 14

N-(1-{[N-cyano-2-(2-methylphenyl)ethanimidoyl]amino}-2,2-dimethylpropyl)-2-[4-(ethylthio)phenyl]acetamide

Example 14A

2-[4-(ethylthio)phenyl]acetamide

The title compound was prepared using the procedure as described in Example 13A, substituting [4-(Ethylthio)phenyl]acetic acid for 2-(3,4-difluorophenyl)acetic acid. MS (ESI$^+$) m/z 213 (M+NH$_3$)$^+$.

Example 14B

N-[1-(1H-1,2,3-benzotriazol-1-yl)-2,2-dimethylpropyl]-2-[4-(ethylthio)phenyl]acetamide The title compound was prepared using the procedure as described in Example 1A, substituting Example 14A for phenylacetamide. MS (ESI$^+$) m/z 383.

Example 14C

N-(1-{[N-cyano-2-(2-methylphenyl)ethanimidoyl]amino}-2,2-dimethylpropyl)-2-[4-(ethylthio)phenyl]acetamide The title compound was prepared using the procedure as described in Example 1D, substituting Example 14B for Example 1A. mp 196-198° C.; MS (ESI$^+$) m/z 437 (M+H)$^+$; ¹H NMR (300 MHz, DMSO-d$_6$) δ ppm 0.92 (s, 9H) 1.22 (t, J=7.29 Hz, 3H) 2.26 (s, 3H) 2.94 (q, J=7.46 Hz, 2H) 3.49 (s, 2H) 3.83 (s, 2H) 5.63 (t, J=8.65 Hz, 1H) 7.03 (m, 2H) 7.22 (m, 6H) 8.15 (d, J=8.82 Hz, 1H) 8.67 (d, J=8.48 Hz, 1H). Anal. calcd for C$_{25}$H$_{32}$N$_4$OS: C, 68.74; H, 7.39; N, 12.83. Found: C, 68.35; H, 7.47; N, 12.77.

Example 15

N-(1-{[N-cyano-2-(2-methylphenyl)ethanimidoyl]amino}-2,2-dimethylpropyl)-2-[4-(methylthio)phenyl]acetamide

Example 15A

2-[4-(methylthio)phenyl]acetamide

The title compound was prepared using the procedure as described in Ruechardt et al., *Chem. Ber.*, Vol. 100 page 654 (1967).

Example 15B

N-[1-(1H-1,2,3-benzotriazol-1-yl)-2,2-dimethylpropyl]-2-[4-(methylthio)phenyl]acetamide The title compound was prepared using the procedure as described in Example 1A, substituting Example 15A for phenylacetamide. MS (ESI$^+$) m/z 369 (M+H)$^+$.

Example 15C

N-(1-{[N-cyano-2-(2-methylphenyl)ethanimidoyl]amino}-2,2-dimethylpropyl)-2-[4-(methylthio)phenyl]acetamide The title compound was prepared using the procedure as described in Example 1D, substituting Example 15B for Example 1A. mp 201-202° C.; MS (ESI$^+$) m/z 423 (M+H)$^+$; ¹H NMR (300 MHz, DMSO-d$_6$) δ ppm 0.92 (s, 9H) 2.26 (s, 3H) 2.45 (s, 3H) 3.48 (m, 2H) 3.83 (s, 2H) 5.63 (t, J=8.65 Hz, 1H) 7.03 (m, 2H) 7.18 (m, 6H) 8.13 (d, J=8.82 Hz, 1H) 8.66 (d, J=8.81 Hz, 1H). Anal. calcd for C$_{24}$H$_{30}$N$_4$OS: C, 68.21; H, 7.16; N, 13.26. Found: C, 68.09; H, 7.43; N, 13.17.

Example 16

N-(1-{[N-cyano-2-(2-methylphenyl)ethanimidoyl]amino}-2,2-dimethylpropyl)-4-(4-methoxyphenyl)butanamide

Example 16A 4-(4-methoxyphenyl)butanamide

The title compound was prepared using the procedure as described in Ganellin, et al., *Arch. Pharm.* Vol 331 pages 395-404 (1998).

Example 16B

N-[1-(1H-1,2,3-benzotriazol-1-yl)-2,2-dimethylpropyl]-4-(4-methoxyphenyl)butanamide The title compound was prepared using the procedure as described in Example 1A, substituting Example 16A for phenylacetamide. MS (ESI$^+$) m/z 381 (M+H)$^+$.

Example 16C

N-(1-{[N-cyano-2-(2-methylphenyl)ethanimidoyl]amino}-2,2-dimethylpropyl)-4-(4-methoxyphenyl)butanamide The title compound was prepared using the procedure as described in Example 1D, substituting Example 16B for Example 1A. mp 171-172° C.; MS (ESI$^+$) m/z 435 (M+H)$^+$; $^1$H NMR (300 MHz, DMSO-d$_6$) δ ppm 0.92 (s, 9H) 1.76 (m, 2H) 2.16 (t, J=7.12 Hz, 2H) 2.27 (s, 3H) 2.50 (m, 2H) 3.72 (s, 3H) 3.84 (s, 2H) 5.64 (t, J=8.48 Hz, 1H) 6.84 (m, 2H) 7.08 (d, J=8.48 Hz, 4H) 7.18 (m, 2H) 7.91 (d, J=8.81 Hz, 1H) 8.58 (d, J=8.81 Hz, 1H). Anal. calcd for C$_{26}$H$_{34}$N$_4$O$_2$: C, 71.86; H, 7.89; N, 12.89. Found: C, 71.65; H, 8.19; N, 12.82.

Example 17

N-(1-{[N-cyano-2-(2-methylphenyl)ethanimidoyl]amino}-2,2-dimethylpropyl)-5-phenylpentanamide

Example 17A 5-phenylpentanamide

The title compound was prepared using the procedure as described in De Tar et al., *J. Amer. Chem. Soc.* Vol. 68 pages 2025-2028 (1946).

Example 17B

N-[1-(1H-1,2,3-benzotriazol-1-yl)-2,2-dimethylpropyl]-5-phenylpentanamide

The title compound was prepared using the procedure as described in Example 1A, substituting Example 17A for phenylacetamide. MS (ESI$^+$) m/z 365 (M+H)$^+$.

Example 17C

N-(1-{[N-cyano-2-(2-methylphenyl)ethanimidoyl]amino}-2,2-dimethylpropyl)-5-phenylpentanamide The title compound was prepared using the procedure as described in Example 1D, substituting Example 17B for Example 1A. mp 151-152° C.; MS (ESI$^+$) m/z 419 (M+H)$^+$; $^1$H NMR (300 MHz, DMSO-d$_6$) δ ppm 0.91 (s, 9H) 1.54 (m, 4H) 2.18 (m, 2H) 2.27 (s, 3H) 2.57 (t, J=6.95 Hz, 2H) 3.83 (s, 2H) 5.63 (t, J=8.65 Hz, 1H) 7.06 (m, J=2.71 Hz, 2H) 7.17 (d, J=7.12 Hz, 5H) 7.27 (m, 2H) 7.89 (d, J=8.48 Hz, 1H) 8.59 (d, J=8.82 Hz, 1H). Anal. calcd for C$_{26}$H$_{34}$N$_4$O: C, 74.61; H, 8.19, N, 13.39. Found: C, 74.39; H, 8.52; N, 13.35.

Example 18

N-(1-{[N-cyano-2-(2-methylphenyl)ethanimidoyl]amino}-2,2-dimethylpropyl)-2-pyridin-3-ylacetamide

Example 18A 2-pyridin-3-yl-acetamide

The title compound was prepared using the procedure as described in Mayer, Joachim M. et al., *Helvetica Chimica Acta* Vol. 65 pages 1868-84 (1982).

Example 18B

N-[1-(1H-1,2,3-benzotriazol-1-yl)-2,2-dimethylpropyl]-2-pyridin-3-ylacetamide

The title compound was prepared using the procedure as described in Example 1A, substituting Example 18A for phenylacetamide. MS (ESI$^+$) m/z 324 (M+H)$^+$.

Example 18C

N-(1-{[N-cyano-2-(2-methylphenyl)ethanimidoyl]amino}-2,2-dimethylpropyl)-2-pyridin-3-ylacetamide The title compound was prepared using the procedure as described in Example 1D, substituting Example 18B for Example 1A. mp 84-86° C.; MS (ESI$^+$) m/z 378 (M+H)$^+$; $^1$H NMR (300 MHz, DMSO-d$_6$) δ ppm 0.93 (s, 9H) 2.26 (s, 3H) 3.57 (s, 2H) 3.83 (s, 2H) 5.63 (t, J=8.48 Hz, 1H) 7.02 (m, 2H) 7.17 (m, 2H) 7.33 (m, 1H) 7.67 (dt, J=7.80, 2.03 Hz, 1H) 8.27 (d, J=8.48 Hz, 1H) 8.44 (d, J=1.70 Hz, 1H) 8.46 (m, 1H) 8.70 (d, J=8.48 Hz, 1H). Anal. calcd for C$_{22}$H$_{27}$N$_5$O0.03H$_2$O: C, 69.90; H, 7.21; N, 18.53. Found: C, 69.50; H, 87.21, N, 18.18.

Example 19

2-(4-chlorophenyl)-N-(1-{[(cyanoimino)(2-methylphenyl)methyl]amino}-2,2-dimethylpropyl)acetamide

Example 19A ethoxy(2-methylphenyl)methaniminium tetrafluoroborate

The title compound was prepared using the procedure as described as in Weintraub, L. et al., *J. Org. Chem.*, Vol. 33(4) pages 1679-81 (1968). MS (ESI$^+$) m/z 164 (M+H)$^+$.

Example 19B

N'-cyano-2-methylbenzenecarboximidamide

To a solution of Example 19A (2.5 g 10.00 mmol) in 10 ml of absolute ethanol was added a solution of sodium ethoxide (681 mg, 10 mmol) in 3.7 ml of absolute ethanol. The precipitate was filtered and the filtrate was treated with a solution of cyanamide (420 mg, 10 mmol) in 10 ml of absolute ethanol. The reaction mixture was refluxed for 3 days and the solvent removed under reduced pressure. The crude mixture was purified by silica gel chromatography, eluting with a gradient of 0-50% ethyl acetate in methylene chloride to provide the 0.3 g of title compound. MS (ESI$^+$) m/z 160 (M+H)$^+$.

Example 19C 2-(4-chlorophenyl)-N-(1-{[(cyanoimino)(2-methylphenyl)methyl]amino}-2,2-dimethylpropyl)acetamide The title compound was prepared using the procedure as described in Example 1D, substituting Example 19B for Example 1C and substituting Example 2B for Example 1A. mp 109-110° C.; MS (ESI$^+$) m/z 397 (M+H)$^+$; $^1$H NMR (300 MHz, DMSO-d$_6$) δ ppm 0.97 (s, 9H) 2.18 (br. s., 3H) 3.55 (s, 2H) 5.66 (t, J=8.31 Hz, 1H) 7.11 (br. s., 1H) 7.36 (m, 7H) 8.14 (d, J=8.48 Hz, 1H) 9.06 (d, J=8.14 Hz, 1H). Anal. calcd for C$_{22}$H$_{25}$ClN$_4$O: C, 66.57; H, 6.35; N, 14.12. Found: C, 66.45; H, 6.11; N, 14.26.

Example 20

2-(4-chlorophenyl)-N-(1-{[N-cyano-2-(2-methylpyridin-3-yl)ethanimidoyl]amino}-2,2-dimethylpropyl)acetamide Example 20A (2-methylpyridin-3-yl)acetonitrile The title compound was prepared using the procedure as described in Sato, Y. et al. *Chem. Phar. Bull., Vol.* 8 pages 427-435 (1960). MS (ESI$^+$) m/z 133 (M+H)$^+$.

Example 20B ethyl 2-(2-methylpyridin-3-yl)ethanimidoate hydrochloride

Through a stirred solution of Example 20A (1.7 g, 12.86 mmol) in absolute ethanol (0.89 g, 19.35 mmol) and anhydrous methylene chloride (25 ml) was bubbled with hydrogen chloride gas for 20 min. The mixture was allowed to stand overnight in the refrigerator. The product was precipitated with anhydrous ether and filtered to obtain the title compound, which was immediately used in the next step. MS (ESI$^+$) m/z 180 (M+H)$^+$.

Example 20C

N'-cyano-2-(2-methylpyridin-3-yl)ethanimidamide

The title compound was prepared using the procedure as described in Example 19B, substituting Example 20B for Example 19A and using two equivalents of sodium ethoxide. MS (ESI$^+$) m/z 175 (M+H)$^+$.

Example 20D 2-(4-chlorophenyl)-N-(1-{[N-cyano-2-(2-methylpyridin-3-yl)ethanimidoyl]amino}-2,2-dimethylpropyl)acetamide The title compound was prepared using the procedure as described in Example 1D, substituting Example 2B for Example 1A and substituting Example 20C for Example 1C. mp 118-119° C.; MS (ESI$^+$) m/z 412 (M+H)$^+$; $^1$H NMR (300 MHz, DMSO-d$_6$) δ ppm 0.94 (s, 9H) 2.46 (s, 3H) 3.53 (s, 2H) 3.87 (m, 2H) 5.58 (t, J=8.48 Hz, 1H) 7.05 (dd, J=7.80, 4.75 Hz, 1H) 7.32 (m, 5H) 8.25 (d, J=8.14 Hz, 1H) 8.32 (dd, J=4.92, 1.53 Hz, 1H) 8.87 (d, J=8.48 Hz, 1H). Anal. calcd for C$_{22}$H$_{26}$ClN$_5$O0.2H$_2$O: C, 63.59; H, 6.40; N, 16.85. Found: C, 63.21; H, 6.35; N, 16.73.

Example 21

N-(1-{[N-cyano-2-(2-methylpyridin-3-yl)ethanimidoyl]amino}-2,2-dimethylpropyl)-2-(3,4-dimethoxyphenyl)acetamide The title compound was prepared using the procedure as described in Example 1D, substituting Example 3A for Example 1A and substituting Example 20C for Example 1C. mp 164-165° C.; MS (ESI$^+$) m/z 438 (M+H)$^+$; $^1$H NMR (300 MHz, DMSO-d$_6$) δ ppm 0.93 (s, 9H) 2.46 (s, 3H) 3.44 (m, 2H) 3.70 (s, 3H) 3.72 (s, 3H) 3.88 (br. s., 2H) 5.59 (t, J=8.48 Hz, 1H) 6.77 (dd, J=8.14, 2.03 Hz, 1H) 6.86 (m, 2H) 7.07 (dd, J=7.80, 4.75 Hz, 1H) 7.36 (dd, J=7.80, 1.36 Hz, 1H) 8.08 (d, J=8.14 Hz, 1H) 8.32 (dd, J=4.92, 1.53 Hz, 1H) 8.79 (d, J=8.14 Hz, 1H). Anal. calcd for C$_{24}$H$_{31}$N$_5$O$_3$: C, 65.88; H, 7.14; N, 16.01. Found: C, 65.66; H, 7.24; N, 15.95.

Example 22

N-(1-{[N-cyano-2-(2-methylpyridin-3-yl)ethanimidoyl]amino}-2,2-dimethylpropyl)-2-quinolin-6-ylacetamide The title compound was prepared using the procedure as described in Example 1D, substituting Example 10B for Example 1A and substituting Example 20C for Example 1C. mp 132-134° C.; MS (ESI$^+$) m/z 434 (M+H$^+$); $^1$H NMR (300 MHz, DMSO-d$_6$) δ ppm 2.44 (s, 3H) 3.76 (s, 2H) 3.84 (d, J=16.28 Hz, 1H) 3.90 (d, J=15.00 Hz, 1H) 5.62 (t, J=8.31 Hz, 1H) 6.90 (dd, J=7.80, 4.75 Hz, 1H) 7.33 (dd, J=7.63, 1.19 Hz, 1H) 7.51 (dd, J=8.31, 4.24 Hz, 1H) 7.67 (dd, J=8.48, 2.03 Hz, 1H) 7.80 (d, J=1.36 Hz, 1H) 7.95 (d, J=8.82 Hz, 1H) 8.23 (dd, J=4.92, 1.53 Hz, 1H) 8.27 (dd, J=8.48, 1.02 Hz, 1H) 8.35 (d, J=8.14 Hz, 1H) 8.86 (dd, J=4.41, 1.70 Hz, 1H) 8.91 (m, 1H).

Example 23

2-(4-chlorophenyl)-N-(1-{[N-cyano-2-quinolin-5-ylethanimidoyl]amino}-2,2-dimethylpropyl)acetamide Example 23A quinolin-5-ylacetonitrile The title compound was prepared using the procedure as described in Engler, T. et al., A.; *Tetrahedron. Lett., Vol.* 44 pages 2903-2905, (2003).

Example 23B ethyl 2-quinolin-5-ylethanimidoate hydrochloride

The title compound was prepared using the procedure as described in Example 20B, substituting Example 23A for Example 20A. MS (ESI+) m/z 215 (M+H)+.

Example 23C

N'-cyano-2-quinolin-5-ylethanimidamide

The title compound was prepared using the procedure as described in Example 19B, substituting Example 23B for Example 19A and using two equivalents of sodium ethoxide. MS (ESI+) m/z 211 (M+H)+.

Example 23D 2-(4-chlorophenyl)-N-(1-{[N-cyano-2-quinolin-5-ylethanimidoyl]amino}-2,2-dimethylpropyl)acetamide The title compound was prepared using the procedure as described in Example 1D, substituting Example 2B for Example 1A and substituting Example 23C for Example 1C. mp 186-188° C.; MS (ESI+) m/z 448 (M+H)+; $^1$H NMR (300 MHz, DMSO-d$_6$) δ ppm 0.93 (s, 9H) 3.55 (s, 2H) 4.35 (d, J=16.27 Hz, 1H) 4.42 (d, J=16.27 Hz, 1H) 5.66 (t, J=8.48 Hz, 1H) 7.28 (m, J=2.71 Hz, 1H) 7.29 (d, J=8.82 Hz, 1H) 7.35 (d, J=8.82 Hz, 1H) 7.57 (m, 1H) 7.60 (dd, J=5.09, 3.73 Hz, 1H) 7.95 (d, J=8.48 Hz, 1H) 8.24 (d, J=8.48 Hz, 1H) 8.55 (d, J=8.14 Hz, 1H) 8.89 (d, J=8.14 Hz, 1H) 8.95 (dd, J=4.24, 1.53 Hz, 1H).

Example 24

N-(1-{[(cyanoimino)(quinolin-5-yl)methyl]amino}-2,2-dimethylpropyl)-2-(3,4-dimethoxyphenyl)acetamide

Example 24A quinoline-5-carbonitrile

The title compound was prepared using the procedure as described in Wagner, G. and Vieweg, H. *Pharmazie* Vol. 31 pages 145-148 (1976).

Example 24B

N'-cyanoquinoline-5-carboximidamide

A mixture of Example 24A (750 mg, 4.81 mmol) and sodium cyanamide (312 mg, 4.81 mmol) in ethanol (10 mL) was heated at reflux for 10 hours and cooled to ambient temperature. The solvent was removed under reduced pressure and the crude mixture was purified by silica gel chromatography, eluting with a gradient of 0-6% of methanol/methylene chloride to provide 0.3 g of the title compound. MS (ESI+) m/z 197 (M+H)+.

Example 24C

N-(1-{[(cyanoimino)(quinolin-5-yl)methyl]amino}-2,2-dimethylpropyl)-2-(3,4-dimethoxyphenyl)acetamide The title compound was prepared using the procedure as described in Example 1D, substituting Example 3A for Example 1A and substituting Example 24B for Exmaple 1C. mp 203-205° C.; MS (ESI+) m/z 460 (M+H)+; $^1$H NMR (300 MHz, DMSO-d$_6$) δ ppm 1.01 (s, 9H) 3.50 (s, 2H) 3.65 (s, 3H) 3.72 (s, 3H) 5.73 (t, J=8.14 Hz, 1H) 6.83 (m, 3H) 7.39 (m, 1H) 7.62 (d, J=7.12 Hz, 1H) 7.85 (dd, J=8.48, 7.12 Hz, 1H) 8.07 (d, J=8.14 Hz, 1H) 8.17 (m, 2H) 8.97 (m, 1H) 9.38 (d, J=8.14 Hz, 1H).

Example 25

2-(4-chlorophenyl)-N-(1-{[(cyanoimino)(quinolin-5-yl)methyl]amino}-2,2-dimethylpropyl)acetamide The title compound was prepared using the procedure as described in Example 1D, substituting Example 2B for Example 1A and substituting Example 24B for Example 1C. mp 218-220° C.; MS (ESI+) m/z 442 (M+H)+; $^1$H NMR (300 MHz, DMSO-d$_6$) δ ppm 1.03 (s, 9H) 3.60 (s, 2H) 5.73 (t, J=8.14 Hz, 1H) 7.05 (m, 1H) 7.34 (m, 4H) 7.62 (d, J=7.80 Hz, 1H) 7.87 (t, J=7.80 Hz, 1H) 8.04 (d, J=8.14 Hz, 1H) 8.17 (d, J=8.14 Hz, 1H) 8.32 (d, J=8.14 Hz, 1H) 8.97 (m, 1H) 9.40 (d, J=9.15 Hz, 1H).

Example 26

N'-cyano-2-(2-methylphenyl)-N-[(1R)-1-phenylethyl]ethanimidamide

Example 26A ethyl 2-(2-methylphenyl)ethanimidoate hydrochloride

The title compound was prepared using the procedure as described in Ife, R. J. et al. (WO 9315055).

Example 26B ethyl N-cyano-2-(2-methylphenyl)ethanimidoate

A solution of Example 26A (15 g, 70.2 mmol) in absolute ethanol (200 mL) was treated with a solution of cyanamide (2.95 g, 70.2 mmol) in dry ether (40 mL) and stirred at room temperature for 72 h. The resulting precipitate was filtered and the solution was concentrated to dryness under reduced pressure to give 10.2 g of the title compound.

Example 26C

N'-cyano-2-(2-methylphenyl)-N-[(1R)-1-phenylethyl]ethanimidamide

A solution of Example 26B (142 mg, 0.7 mmol) and (R)-1-phenylethylamine (85 mg, 0.7 mmol) in absolute ethanol (1 mL) was stirred at 60° C. for 6 h. The mixture was concentrated under reduced pressure and purified by preparative HPLC on a Waters Symmetry C8 column (40 mm×100 mm, 7 µm particle size) using a gradient of 10% to 100% acetonitrile in 10 mM of ammonium acetate over 15 min at a flow rate of 70 mL/min to provide the title compound. MS (ESI+) m/z 277 (M+H)+; 1H NMR (300 MHz, DMSO-d6) δ ppm 1.46 (d, J=6.78 Hz, 3H) 2.28 (s, 3H) 3.83 (s, 2H) 5.10 (m, 1H) 6.95 (d, J=8.48 Hz, 1H) 7.16 (m, 3H) 7.29 (m, 1H) 7.35 (m, 5H) 9.37 (d, J=7.46 Hz, 1H).

Example 27

N'-cyano-N-[(1R)-2,3-dihydro-1H-inden-1-yl]-2-(2-methylphenyl)ethanimidamide

The title compound was prepared using the procedure as described in Example 26C, substituting (1R)-2,3-dihydro-1H-inden-1-ylamine for (R)-1-phenylethylamine. MS (ESI+) m/z 290 (M+H)+; 1H NMR (300 MHz, DMSO-d6) δ ppm 1.92 (m, 2H) 2.31 (s, 3H) 2.47 (m, 1H) 2.88 (m, 1H) 2.99 (m, 1H) 3.86 (s, 2H) 5.49 (q, J=7.46 Hz, 1H) 7.12-7.32 (m, 8H) 9.32 (d, J=7.46 Hz, 1H).

Example 28

N'-cyano-2-(2-methylphenyl)-N-(1-methyl-1-phenylethyl)ethanimidamide

The title compound was prepared using the procedure as described in Example 26C, substituting 1-methyl-1-phenylethylamine for (R)-1-phenylethylamine. MS (ESI+) m/z 292 (M+H)+; 1H NMR (300 MHz, DMSO-d6) δ ppm 2.30 (s, 6H) 3.82 (s, 2H) 7.03 (m, 2H) 7.20 (m, 4H) 7.34 (d, J=4.07 Hz, 3H) 9.11 (s, 1H).

Example 29

N'-cyano-N-[(1R)-1-(4-fluorophenyl)ethyl]-2-(2-methylphenyl)ethanimidamide

The title compound was prepared using the procedure as described in Example 26C, substituting (1R)-1-(4-fluorophenyl)ethanamine for (R)-1-phenylethylamine. MS (ESI+) m/z 296 (M+H)+; 1H NMR (300 MHz, DMSO-d6) δ ppm 1.45 (d, J=6.78 Hz, 3H) 2.28 (s, 3H) 3.82 (s, 2H) 5.10 (m, 1H) 6.95 (m, 1H) 7.19 (m, 5H) 7.39 (dd, J=8.48, 5.42 Hz, 2H) 9.36 (d, J=7.46 Hz, 1H).

Example 30

N'-cyano-2-(2-methylphenyl)-N-[(1R)-1-phenylpropyl]ethanimidamide

The title compound was prepared using the procedure as described in Example 26C, substituting (1R)-1-phenylpropan-1-amine for (R)-1-phenylethylamine. MS (ESI+) m/z 292 (M+H)+; 1H NMR (300 MHz, DMSO-d6) δ ppm 0.87 (t, J=7.29 Hz, 3H) 1.81 (m, 2H) 2.28 (s, 3H) 3.84 (s, 2H) 4.86 (m, 1H) 6.92 (d, J=7.12 Hz, 1H) 7.16 (m, 4H) 7.34 (m, 4H) 9.35 (d, J=7.80 Hz, 1H).

Example 31

N'-cyano-2-(2-methylphenyl)-N-[1-thien-2-ylethyl]ethanimidamide

The title compound was prepared using the procedure as described in Example 26C, substituting 1-thien-2-ylethanamine for (R)-1-phenylethylamine. MS (ESI+) m/z 284 (M+H)+; 1H NMR (300 MHz, DMSO-d6) δ ppm 1.56 (d, J=6.78 Hz, 3H) 2.28 (s, 3H) 3.82 (m, 2H) 5.40 (m, 1H) 7.01 (m, 2H) 7.06 (m, 2H) 7.17 (m, 3H) 7.46 (dd, J=5.09, 1.36 Hz, 1H) 9.42 (d, J=7.80 Hz, 1H).

Example 32

N'-cyano-N-[(1R)-1-(2-fluorophenyl)ethyl]-2-(2-methylphenyl)ethanimidamide

The title compound was prepared using the procedure as described in Example 26C, substituting (1R)-1-(2-fluorophenyl)ethanamine for (R)-1-phenylethylamine. MS (ESI+) m/z 296 (M+H)+; 1H NMR (300 MHz, DMSO-d6) δ ppm 1.47 (d, J=7.12 Hz, 3H) 2.28 (s, 3H) 3.83 (s, 2H) 5.29 (m, 1H) 6.95 (m, 1H) 7.12 (m, 1H) 7.19 (m, 3H) 7.37 (m, 3H) 9.43 (d, J=4.41 Hz, 1H).

Example 33

N'-cyano-N-[1-(3-fluorophenyl)ethyl]-2-(2-methylphenyl)ethanimidamide

The title compound was prepared using the procedure as described in Example 26C, substituting 1-(3-fluorophenyl)ethanamine for (R)-1-phenylethylamine. MS (ESI+) m/z 296 (M+H)+; 1H NMR (300 MHz, DMSO-d6) δ ppm 1.45 (d, J=7.12 Hz, 3H) 2.29 (s, 3H) 3.84 (s, 2H) 5.12 (m, 1H) 6.97 (m, 1H) 7.13 (m, 3H) 7.20 (m, 4H) 7.42 (m, 1H) 9.38 (d, J=7.12 Hz, 1H).

Example 34

N'-cyano-N-[1-(3,5-difluorophenyl)ethyl]-2-(2-methylphenyl)ethanimidamide

The title compound was prepared using the procedure as described in Example 26C, substituting 1-(3,5-difluorophenyl)ethanamine for (R)-1-phenylethylamine. MS (ESI+) m/z 314 (M+H)+; 1H NMR (300 MHz, DMSO-d6) δ ppm 1.44 (d, J=7.12 Hz, 2H) 2.29 (s, 3H) 3.85 (s, 2H) 5.12 (m, 1H) 6.98 (m, 1H) 7.06 (m, 2H) 7.17 (m, 2H) 7.21 (m, 2H) 9.37 (d, J=7.12 Hz, 1H).

Example 35

N'-cyano-N-[3-(4-methoxyphenyl)-1-methylpropyl]-2-(2-methylphenyl)ethanimidamide The title compound was prepared using the procedure as described in Example 26C, substituting 3-(4-methoxyphenyl)-1-methylpropylamine for (R)-1-phenylethylamine. mp 103-104° C.; MS (ESI+) m/z 336 (M+H)+; 1H NMR (300 MHz, DMSO-d6) δ ppm 1.16 (d, J=6.44 Hz, 3H) 1.73 (m, 2H) 2.32 (s, 3H) 2.54 (m, 2H) 3.72 (s, 3H) 3.80 (s, 2H) 3.93 (m, 1H) 6.85 (m, 2H) 7.09 (m, 3H) 7.21 (m, 3H) 8.85 (d, J=7.46 Hz, 1H). Anal. calcd for $C_{21}H_{25}N_3O$: C, 75.19; H, 7.51; N, 12.53; O, 4.77. Found: C, 74.96; H, 7.79; N, 12.34.

Example 36

N'-cyano-2-(2-methylphenyl)-N-[(1R)-1-phenylpropyl]ethanimidamide

The title compound was prepared using the procedure as described in Example 26C, substituting (R)-1-phenylpropylamine for (R)-1-phenylethylamine. MS (ESI+) m/z 292 (M+H)+; 1H NMR (300 MHz, DMSO-d6) δ ppm 0.87 (t, J=7.12 Hz, 3H) 1.78 (m, 2H) 2.28 (s, 3H) 3.84 (s, 2H) 4.86 (m, 1H) 6.92 (m, 2H) 7.24 (m, 7H) 9.35 (d, J=7.80 Hz, 1H).

Example 37

N-cyano-2-(2-methylphenyl)-N-[(1R)-1,2,3,4-tetrahydronaphthalen-1-yl]ethanimidamide The title compound was prepared using the procedure as described in Example 26C, substituting (1R)-1,2,3,4-tetrahydronaphthalen-1-amine for (R)-1-phenylethylamine. MS (ESI$^+$) m/z 304 (M+H)$^+$; $^1$H NMR (300 MHz, DMSO-d$_6$) δ ppm 1.86 (m, 4H) 2.30 (s, 3H) 2.75 (m, 2H) 3.85 (s, 2H) 5.18 (m, 1H) 7.17 (m, 8H) 9.31 (d, J=7.80 Hz, 1H).

Example 38

N-[2-(2-chlorophenyl)-2-(dimethylamino)ethyl]-N'-cyano-2-(2-methylphenyl)ethanimidamide The title compound was prepared using the procedure as described in Example 26C, substituting 1-(2-chlorophenyl)-N$^1$,N$^1$-dimethylethane-1,2-diamine for (R)-1-phenylethylamine. MS (ESI$^+$) m/z 355 (M+H)$^+$; $^1$H NMR (300 MHz, DMSO-d$_6$) δ ppm 2.15 (s, 6H) 2.20 (s, 3H) 3.59 (m, 1H) 3.76 (s, 2H) 3.84 (m, 1H) 4.29 (t, J=6.78 Hz, 1H) 6.85 (m, 1H) 7.07 (m, 1H) 7.16 (m, 2H) 7.34 (m, 2H) 7.46 (m, 2H) 8.65 (m, 1H).

Example 39

N'-cyano-N-[1-(4-fluorophenyl)ethyl]-2-(2-methylphenyl)ethanimidamide

The title compound was prepared using the procedure as described in Example 26C, substituting 1-(4-fluorophenyl)ethanamine for (R)-1-phenylethylamine. MS (ESI$^+$) m/z 296 (M+H)$^+$; $^1$H NMR (300 MHz, DMSO-d$_6$) δ ppm 1.45 (d, J=7.12 Hz, 3H) 2.28 (s, 3H) 3.82 (s, 2H) 5.10 (m, 1H) 6.93 (m, 1H) 7.16 (m, 5H) 7.39 (m, 2H) 9.37 (d, J=7.80 Hz, 1H).

Example 40

N'-cyano-N-(5-fluoro-2,3-dihydro-1H-inden-1-yl)-2-(2-methylphenyl)ethanimidamide The title compound was prepared using the procedure as described in Example 26C, substituting 5-fluoro-2,3-dihydro-1H-inden-1-ylamine for (R)-1-phenylethylamine. MS (ESI$^+$) m/z 308 (M+H)$^+$; $^1$H NMR (300 MHz, DMSO-d$_6$) δ ppm 1.95 (m, 1H) 2.30 (s, 3H) 2.55 (m, 1H) 2.86 (m, 1H) 2.99 (m, 1H) 3.84 (s, 2H) 5.44 (m, 1H) 7.04 (m, 1H) 7.11 (m, 2H) 7.20 (m, 3H) 7.32 (m, 1H) 9.31 (d, J=7.80 Hz, 1H). Anal. calcd for C$_{14}$H$_8$ClN$_4$: C, 74.25; H, 5.90; N, 13.67. Found: C, 74.19; H, 5.98; N, 13.87.

Example 41

N'-cyano-N-(1,1-dimethyl-1,2,3,4-tetrahydronaphthalen-2-yl)-2-(2-methylphenyl)ethanimidamide The title compound was prepared using the procedure as described in Example 26C, substituting 1,1-dimethyl-1,2,3,4-tetrahydronaphthalen-2-amine for (R)-1-phenylethylamine. MS (ESI$^+$) m/z 330 (M+H)$^+$; $^1$H NMR (300 MHz, DMSO-d$_6$) δ ppm 1.25 (s, 3H) 1.29 (s, 3H) 1.95 (m, 2H) 2.30 (s, 3H) 2.84 (m, 2H) 3.90 (s, 2H) 4.21 (m, 1H) 7.13 (m, 7H) 7.36 (m, 2H) 8.76 (d, J=8.81 Hz, 1H).

Example 42

N-[2-(2-chlorophenyl)ethyl]-N'-cyano-2-(2-methylphenyl)ethanimidamide

The title compound was prepared using the procedure as described in Example 26C, substituting 2-(2-chlorophenyl)ethanamine for (R)-1-phenylethylamine. MS (ESI$^+$) m/z 312 (M+H)$^+$; $^1$H NMR (300 MHz, DMSO-d$_6$) δ ppm 2.25 (s, 3H) 2.96 (t, J=7.12 Hz, 2H) 3.54 (m, 2H) 3.79 (s, 2H) 6.99 (m, 1H) 7.22 (m, 6H) 7.44 (m, 1H) 8.84 (br. s., 1H).

Example 43

N-(4-chloro-2,3-dihydro-1H-inden-1-yl)-N'-cyano-2-(2-methylphenyl)ethanimidamide The title compound was prepared using the procedure as described in Example 26C, substituting 4-chloro-2,3-dihydro-1H-inden-1-ylamine for (R)-1-phenylethylamine. MS (ESI$^+$) m/z 322 (M+H)$^+$; $^1$H NMR (300 MHz, DMSO-d$_6$) δ ppm 1.96 (m, 1H) 2.31 (s, 3H) 2.56 (m, 1H) 2.94 (m, 2H) 3.85 (s, 2H) 5.57 (m, 1H) 7.24 (m, 7H) 9.35 (d, J=7.80 Hz, 1H).

Example 44

N'-cyano-2-(2-methylphenyl)-N-(2-morpholin-4-yl-1-phenylethyl)ethanimidamide

The title compound was prepared using the procedure as described in Example 26C, substituting 2-morpholin-4-yl-1-phenylethanamine for (R)-1-phenylethylamine. MS (ESI$^+$) m/z 363 (M+H)$^+$; $^1$H NMR (300 MHz, DMSO-d$_6$) δ ppm 2.32 (s, 3H) 2.37 (m, 2H) 2.51 (m, 2H) 2.77 (m, 2H) 3.58 (m, 4H) 3.86 (ABq, 2H, J=15.60 Hz, Δν$_{AB}$=26 Hz) 3.92 (d, J=15.60 Hz, 1H) 5.20 (m, 1H) 7.26 (m, 9H) 9.30 (d, J=7.80 Hz, 1H).

Example 45

N'-cyano-2-(2-methylphenyl)-N-[(1R,2R,4R)-1,2,3,4-tetrahydro-1,4-methanonaphthalen-2-yl]ethanimidamide The title compound was prepared using the procedure as described in Example 26C, substituting (1R,2R,4R)-1,2,3,4-tetrahydro-1,4-methanonaphthalen-2-amine for (R)-1-phenylethylamine. MS (ESI$^+$) m/z 316 (M+H)$^+$; $^1$H NMR (300 MHz, DMSO-d$_6$) δ ppm 1.76 (m, 4H) 2.33 (s, 3H) 3.39 (s, 2H) 3.69 (m, 1H) 3.83 (s, 2H) 7.07 (m, 3H) 7.23 (m, 5H) 9.21 (d, J=7.12 Hz, 1H).

Example 46

N'-cyano-N-[(1S,2S,4S)-6,7-dimethoxy-1,2,3,4-tetrahydro-1,4-methanonaphthalen-2-yl]-2-(2-methylphenyl)ethanimidamide The title compound was prepared using the procedure as described in Example 26C, substituting (1S,2S,4S)-6,7-dimethoxy-1,2,3,4-tetrahydro-1,4-methanonaphthalen-2-amine for (R)-1-phenylethylamine. MS (ESI$^+$) m/z 376 (M+H)$^+$; $^1$H NMR (300 MHz, DMSO-d$_6$) δ ppm 1.71 (m, 4H) 2.33 (s, 3H) 3.29 (m, 2H) 3.66 (m, 1H) 3.71 (s, 3H) 3.73 (s, 3H) 3.83 (s, 2H) 6.88 (m, 1H) 6.96 (m, 1H) 7.06 (m, 1H) 7.20 (m, 3H) 9.17 (d, J=6.44 Hz, 1H).

Example 47

N'-cyano-2-(2-methylphenyl)-N-(1-pyridin-4-ylpentyl)ethanimidamide

The title compound was prepared using the procedure as described in Example 26C, substituting 1-pyridin-4-ylpentan-1-amine for (R)-1-phenylethylamine. MS (ESI$^+$) m/z 321 (M+H)$^+$; $^1$H NMR (300 MHz, DMSO-d$_6$) δ ppm 0.84 (t, J=6.78 Hz, 3H) 1.28 (m, 4H) 1.74 (m, 2H) 2.28 (s, 3H) 3.87 (s, 2H) 4.92 (m, 1H) 6.93 (m, 1H) 7.17 (m, 3H) 7.33 (m, 2H) 8.55 (m, 2H) 9.41 (d, J=7.80 Hz, 1H).

Example 48

N'-cyano-2-(2-methylphenyl)-N-(1-pyridin-4-ylpropyl)ethanimidamide

The title compound was prepared using the procedure as described in Example 26C, substituting 1-pyridin-4-ylpropan-1-amine for (R)-1-phenylethylamine. MS (ESI$^+$) m/z 293 (M+H)$^+$; $^1$H NMR (300 MHz, DMSO-d$_6$) δ ppm 0.89 (t, J=7.12 Hz, 3H) 1.79 (m, 2H) 2.29 (s, 3H) 3.88 (s, 2H) 4.87 (m, 1H) 6.94 (m, 1H) 7.17 (m, 3H) 7.33 (m, 2H) 8.55 (m, 2H) 9.43 (d, J=6.78 Hz, 1H).

Example 49

N'-cyano-2-(2-methylphenyl)-N-[1-(2-morpholin-4-ylphenyl)ethyl]ethanimidamide

Example 49A 1-(2-morpholin-4-ylphenyl)ethanone

The title compound was prepared using the procedure as described in Moehrle, H.; et al., *Chemical Sciences Vol.* 53(11) pages 1369-1378 (1998).

Example 49B 1-(2-morpholin-4-ylphenyl)ethanone O-methyloxime

A mixture of Example 49A (1.22 g, 5.94 mmol) and methoxyamine hydrochloride (550 mg, 6.59 mmol) in pyridine (20 mL) was stirred at room temperature for 12 h. The reaction was diluted with ethyl acetate and washed sequentially with 3 N HCl, 1 N HCl and brine. The organic layer was dried over anhydrous magnesium sulfate, filtered and concentrated to dryness under reduced pressure to give 1.3 g of the title compound. MS (ESI$^+$) m/z 235 (M+H)$^+$.

Example 49C 1-(2-morpholin-4-ylphenyl)ethanamine

A mixture of Example 49B (1.3 g, 5.54 mmol) and Raney nickel (14 g) in a mixture of 20% NH$_3$ in methanol (140 mL) was hydrogenated at 60 psi for 11 hrs. The reaction was filtered and concentrated to dryness under reduced pressure to give 1.1 g of the title compound. MS (ESI$^+$) m/z 207 (M+H)$^+$.

Example 49D

N'-cyano-2-(2-methylphenyl)-N-[1-(2-morpholin-4-ylphenyl)ethyl]ethanimidamide

The title compound was prepared using the procedure as described in Example 26C, substituting Example 49C for (R)-1-phenylethylamine. MS (ESI$^+$) m/z 363 (M+H)$^+$; $^1$H NMR (300 MHz, DMSO-d$_6$) δ ppm 1.41 (d, J=6.78 Hz, 3H) 2.28 (s, 3H) 2.70 (m, 2H) 3.00 (m, 2H) 3.74 (m, 4H) 3.82 (s, 2H) 5.61 (m, 1H) 6.98 (m, 1H) 7.24 (m, 7H) 9.29 (d, J=7.46 Hz, 1H). Anal. calcd for C$_{22}$H$_{26}$N$_4$O 0.15H$_2$O: C, 72.41; H, 7.26; N, 15.35. Found: C, 72.11; H, 7.11; N, 15.33.

Example 50

N'-cyano-N-[(1R)-2,3-dihydro-1H-inden-1-yl]-2-(2-fluorophenyl)ethanimidamide

Example 50A ethyl 2-(2-fluorophenyl)ethanimidoate hydrochloride

The title compound was prepared using the procedure as described in Kelley, James L. et al., *Journal of Medicinal Chemistry Vol.* 38(18) pages 3676-9 (1995).

Example 50B ethyl N-cyano-2-(2-fluorophenyl)ethanimidoate

The title compound was prepared using the procedure as described in Example 26B, substituting Example 50A for Example 26A. MS (ESI/NH$_3$) m/z 206 (M+H)$^+$.

Example 50C

N'-cyano-N-[(1R)-2,3-dihydro-1H-inden-1-yl]-2-(2-fluorophenyl)ethanimidamide

The title compound was prepared using the procedure as described in Example 26C, substituting Example 50B for Example 26B, and substituting (1R)-2,3-dihydro-1H-inden-1-ylamine for (R)-1-phenylethylamine. mp 141-142° C.; MS (ESI$^+$) m/z 294 (M+H)$^+$; $^1$H NMR (300 MHz, DMSO-d$_6$) δ ppm 1.91 (m, 1H) 2.49 (m, 1H) 2.92 (m, 2H) 3.93 (s, 2H) 5.44 (m, 1H) 7.28 (m, 8H) 9.39 (d, J=6.44 Hz, 1H). Anal. calcd for C$_{14}$H$_8$ClN$_4$: C, 73.70; H, 5.50; N, 14.32. Found: C, 73.86; H, 5.49; N, 14.24.

Example 51

2-(2-chlorophenyl)-N'-cyano-N-(5-fluoro-2,3-dihydro-1H-inden-1-yl)ethanimidamide Example 51A ethyl 2-(2-chlorophenyl)ethanimidoate hydrochloride The title compound was prepared using the procedure as described in Ife, R. et al. (WO 9315055).

Example 51B ethyl 2-(2-chlorophenyl)-N-cyanoethanimidoate

The title compound was prepared using the procedure as described in Example 26B, substituting Example 51A for Example 26A. MS (ESI/NH$_3$) m/z 222 (M+H)$^+$.

Example 51C 2-(2-chlorophenyl)-N'-cyano-N-(5-fluoro-2,3-dihydro-1H-inden-1-yl)ethanimidamide The title compound was prepared using the procedure as described in Example 26C, substituting 5-fluoro-2,3-dihydro-1H-inden-1-ylamine for (R)-1-phenylethylamine. MS (ESI$^+$) m/z 328 (M+H)$^+$; $^1$H NMR (300 MHz, DMSO-d$_6$) δ ppm 1.95 (m, 1H) 2.52 (m, 1H) 2.91 (m, 2H) 4.00 (s, 2H) 5.44 (m, 1H) 7.08 (m, 2H) 7.40 (m, 5H) 9.29 (br. s., 1H).

Example 52

N'-cyano-N-(2-methylbenzyl)-3-phenylbutanimidamide

Example 52A 3-phenylbutyronitrile

The title compound was prepared using the procedure as described in Edwards, M. and Williams, J. *Angewandte Chemie, International Edition Vol.* 41(24) pages 4740-4743 (2002).

Example 52B ethyl 3-phenylbutanimidoate hydrochloride

Through a stirred solution of Example 52A (3.9 g, 26.8 mmol) in absolute ethanol (30 mL) was bubbled with hydrogen chloride gas for 20 min. The mixture was allowed to stand for overnight in the refrigerator. The product was precipitated with anhydrous ether and filtered to obtain 4.8 g of the title compound. MS (ESI/NH$_3$) m/Z 192 (M+H)$^+$.

Example 52C ethyl N-cyano-3-phenylbutanimidoate

The title compound was prepared using the procedure as described in Example 26B, substituting Example 52A for Example 26A. MS (ESI/NH$_3$) m/z 217 (M+H)$^+$.

Example 52D

N'-cyano-N-(2-methylbenzyl)-3-phenylbutanimidamide

A mixture of Example 52C (0.1 g, 0.44 mmol) and 2-methylbenzylamine (0.2 mL) was heated to 90° C. for 2.5 hours. The mixture was cooled down to room temperature and purified by flash chromatography (eluting with 35% ethyl acetate/hexanes) to give the title compound as a white solid. MS (ESI/NH$_3$) m/z 292 (M+H)$^+$; $^1$H NMR (300 MHz, DMSO-d$_6$) δ 1.24-1.26 (d, 3H) 2.17 (s, 3H) 2.79-2.82 (d, 2H) 3.38-3.40 (m, 1H) 4.25-4.29 (m, 2H) 7.08-7.32 (m, 9H) 9.01 (t, 1H).

Example 53

N'-cyano-2-(2-methylpyridin-3-yl)-N-[(1R)-1-phenylethyl]ethanimidamide

Example 53A (2-methylpyridin-3-yl)acetonitrile

The title compound was prepared using the procedure as described in Murata, et al. (WO9206978).

Example 53B ethyl 2-(2-methylpyridin-3-yl)ethanimidoate hydrochloride

Through a stirred solution of Example 53A (1.7 g, 12.86 mmol), absolute ethanol (0.89 g, 19.35 mmol) and anhydrous methylene chloride (25 ml) was bubbled with hydrogen chloride gas for 20 min. The mixture was allowed to stand overnight in the refrigerator. The product was precipitated with anhydrous ether and filtered to obtain the title compound, which was immediately used in the next step. MS (ESI$^+$) m/z 180 (M+H)$^+$.

Example 53C ethyl N-cyano-2-(2-methylpyridin-3-yl)ethanimidoate

The title compound was prepared using the procedure as described in Example 26B, substituting Example 53B for Example 26A. MS (ESI$^+$) m/z 175 (M+H)$^+$.

Example 53D

N'-cyano-2-(2-methylpyridin-3-yl)-N-[(1R)-1-phenylethyl]ethanimidamide

The title compound was prepared using the procedure as described in Example 26C, substituting Example 53C for Example 26B. MS (ESI$^+$) m/z 278 (M+H)$^+$; $^1$H NMR (300 MHz, DMSO-d$_6$) δ ppm 1.46 (d, J=7.12 Hz, 3H) 2.47 (s, 3H) 3.89 (s, 2H) 5.09 (m, 1H) 7.18 (dd, J=7.80, 4.75 Hz, 1H) 7.35 (s, 6H) 8.34 (dd, J=4.92, 1.53 Hz, 1H) 9.43 (d, J=7.46 Hz, 1H).

Example 54

N'-cyano-N-[(1R)-2,3-dihydro-1H-inden-1-yl]-2-(2-methylpyridin-3-yl)ethanimidamide The title compound was prepared using the procedure as described in Example 26C, substituting Example 53C for Example 26B, and substituting (1R)-2,3-dihydro-1H-inden-1-ylamine for (R)-1-phenylethylamine. MS (ESI$^+$) m/z 290 (M+H)$^+$; $^1$H NMR (300 MHz, DMSO-d$_6$) δ ppm 1.90 (m, 1H) 2.47 (m, 1H) 2.48 (s, 3H) 2.88 (m, 1H) 2.99 (m, 1H) 3.91 (s, 2H) 5.48 (dd, J=15.00, 7.35 Hz, 1H) 7.27 (m, 5H) 7.51 (dd, J=7.80, 1.70 Hz, 1H) 8.36 (dd, J=4.75, 1.70 Hz, 1H) 9.37 (d, J=6.10 Hz, 1H).

Example 55

N-[2-(2-chlorophenyl)ethyl]-N'-cyano-2-(2-methylpyridin-3-yl)ethanimidamide

The title compound was prepared using the procedure as described in Example 26C, substituting Example 53C for Example 26B, and substituting 2-(2-chlorophenyl)ethanamine for (R)-1-phenylethylamine. MS (ESI$^+$) m/z 318 (M+H)$^+$; $^1$H NMR (300 MHz, DMSO-d$_6$) δ ppm 2.45 (s, 3H) 2.96 (t, J=7.12 Hz, 1H) 3.52 (t, J=7.12 Hz, 1H) 3.57 (t, J=7.12 Hz, 1H) 3.85 (s, 2H) 7.19 (dd, J=7.80, 4.75 Hz, 1H) 7.29 (m, 3H) 7.36 (dd, J=7.80, 1.36 Hz, 1H) 7.44 (m, 1H) 8.36 (dd, J=4.75, 1.70 Hz, 1H) 8.91 (t, J=5.59 Hz, 1H).

Example 56

N'-cyano-N-(5-fluoro-2,3-dihydro-1H-inden-1-yl)-2-(2-methylpyridin-3-yl)ethanimidamide The title compound was prepared using the procedure as described in Example 26C, substituting Example 53C for Example 26B, and substituting 5-fluoro-2,3-dihydro-1H-inden-1-ylamine for (R)-1-phenylethylamine. mp 148-149° C.; MS (ESI$^+$) m/z 310 (M+H)$^+$; $^1$H NMR (300 MHz, DMSO-d$_6$) δ ppm 1.94 (m, 1H) 2.50 (s, 3H) 2.56 (m, 1H) 2.92 (m, 2H) 3.90 (s, 2H) 5.43 (m, 1H) 7.08 (m, 2H) 7.23 (m, 1H) 7.33 (m, 1H) 7.49 (m, 1H) 8.36 (m, 1H) 9.35 (d, J=7.80 Hz, 1H). Anal. calcd for C$_{14}$H$_8$ClN$_4$: C, 70.11; H, 5.56; N, 18.17. Found: C, 69.79; H, 5.57; N, 17.82.

Example 57

N'-cyano-2-(2-methylpyridin-3-yl)-N-[(1R)-1-phenylpropyl]ethanimidamide

The title compound was prepared using the procedure as described in Example 26C, substituting Example 53C for Example 26B, and substituting (1R)-1-phenylpropan-1-amine for (R)-1-phenylethylamine. mp 52-54° C.; MS (ESI$^+$) m/z 293 (M+H)$^+$; $^1$H NMR (300 MHz, DMSO-d$_6$) δ ppm 0.87 (t, J=7.46 Hz, 3H) 1.78 (m, 2H) 2.47 (s, 3H) 3.90 (s, 2H) 4.84 (m, 1H) 7.16 (m, 1H) 7.32 (m, 6H) 8.34 (m, 1H) 9.40 (m, 1H) Anal. calcd for C$_{14}$H$_8$ClN$_4$: C, 73.94; H, 6.89; N, 19.16. Found: C, 73.57; H, 7.16; N, 18.96.

Example 58

N'-cyano-2-(2-methylpyridin-3-yl)-N-[(1R)-1,2,3,4-tetrahydronaphthalen-1-yl]ethanimidamide The title compound was prepared using the procedure as described in Example 26C, substituting Example 53C for Example 26B, and substituting (1R)-1,2,3,4-tetrahydronaphthalen-1-amine for (R)-1-phenylethylamine. mp 193-194° C.; MS (ESI$^+$) m/z 305 (M+H)$^+$; $^1$H NMR (300 MHz, DMSO-d$_6$) δ ppm 1.87 (m, 4H) 2.49 (s, 3H) 2.75 (m, 2H) 3.91 (s, 2H) 5.17 (m, 1H) 7.19 (m, 5H) 7.49 (m, 1H) 8.35 (m, 1H) 9.36 (d, J=7.46 Hz, 1H). Anal. calcd for C$_{14}$H$_8$ClN$_4$: C, 74.97; H, 6.62; N, 18.41. Found: C, 74.60; H, 6.55; N, 18.26.

Example 59

N'-cyano-N-[1-(3,5-difluorophenyl)ethyl]-2-(2-methylpyridin-3-yl)ethanimidamide The title compound was prepared using the procedure as described in Example 26C, substituting Example 53C for Example 26B, and substituting 1-(3,5-difluorophenyl)ethanamine for (R)-1-phenylethylamine. MS (ESI$^+$) m/z 315 (M+H)$^+$; $^1$H NMR (300 MHz, DMSO-d$_6$) δ ppm 1.44 (d, J=7.12 Hz, 3H) 2.48 (s, 3H) 3.92 (s, 2H) 5.11 (m, 1H) 7.08 (m, 2H) 7.15 (m, 1H) 7.20 (dd, J=7.80, 4.75 Hz, 1H) 7.37 (dd, J=7.63, 1.53 Hz, 1H) 8.36 (dd, J=4.75, 1.70 Hz, 1H) 9.40 (d, J=7.46 Hz, 1H).

Example 60

N'-cyano-N-[1-(3-fluorophenyl)ethyl]-2-(2-methylpyridin-3-yl)ethanimidamide

The title compound was prepared using the procedure as described in Example 26C, substituting Example 53C for Example 26B, and substituting 1-(3-fluorophenyl)ethanamine for (R)-1-phenylethylamine. MS (ESI$^+$) m/z 297 (M+H)$^+$; $^1$H NMR (300 MHz, DMSO-d$_6$) δ ppm 1.45 (d, J=7.12 Hz, 3H) 2.48 (s, 3H) 3.90 (s, 2H) 5.11 (m, 1H) 7.19 (m, 3H) 7.40 (s, 2H) 8.35 (dd, J=4.75, 1.70 Hz, 1H) 9.42 (d, J=7.46 Hz, 1H).

Example 61

N'-cyano-N-[(1R)-2,3-dihydro-1H-inden-1-yl]-2-quinolin-5-ylethanimidamide

Example 61A quinolin-5-ylacetonitrile

The title compound was prepared using the procedure as described in Engler, T. A. et al., *Tetrahedron Letters* Vol. 44(14) pages 2903-2905 (2003).

Example 61B ethyl 2-quinolin-5-ylethanimidoate hydrochloride

The title compound was prepared using the procedure as described in Example 53B, substituting Example 61A for Example 53A. MS (ESI$^+$) m/z 214 (M+H)$^+$.

Example 61C ethyl N-cyano-2-quinolin-5-ylethanimidoate

The title compound was prepared using the procedure as described in Example 26B, substituting Example 61B for Example 26A. MS (ESI$^+$) m/z 240 (M+H)$^+$.

Example 61D

N'-cyano-N-[(1R)-2,3-dihydro-1H-inden-1-yl]-2-quinolin-5-ylethanimidamide

The title compound was prepared using the procedure as described in Example 26C, substituting Example 61C for Example 26B and substituting (1R)-2,3-dihydro-1H-inden-1-ylamine for (R)-1-phenylethylamine. MS (ESI$^+$) m/z 327 (M+H)$^+$; $^1$H NMR (300 MHz, DMSO-d$_6$) δ ppm 1.89 (m, 1H) 2.54 (m, 1H) 2.89 (m, 1H) 2.99 (m, 1H) 4.41 (s, 2H) 5.53 (dd, J=15.00, 7.35 Hz, 1H) 7.28 (m, 4H) 7.48 (d, J=7.80 Hz, 1H) 7.62 (dd, J=8.65, 4.24 Hz, 1H) 7.77 (dd, J=8.48, 7.12 Hz, 1H) 7.99 (d, J=8.48 Hz, 1H) 8.57 (m, 1H) 8.96 (dd, J=4.07, 1.70 Hz, 1H) 9.45 (d, J=7.46 Hz, 1H).

Example 62

N'-cyano-N-[(1S)-2,3-dihydro-1H-inden-1-yl]-2-quinolin-5-ylethanimidamide

The title compound was prepared using the procedure as described in Example 26C, substituting Example 61C for Example 26B and substituting (1S)-2,3-dihydro-1H-inden-1-ylamine for (R)-1-phenylethylamine. MS (ESI$^+$) m/z 327 (M+H)$^+$; $^1$H NMR (300 MHz, DMSO-d$_6$) δ ppm 1.91 (m, 1H) 2.54 (m, 1H) 2.89 (m, 1H) 2.99 (m, 1H) 4.41 (s, 1H) 5.53 (dd, J=15.00, 7.46 Hz, 1H) 7.29 (m, 4H) 7.48 (dd, J=7.12, 0.68 Hz, 1H) 7.62 (dd, J=8.65, 4.24 Hz, 1H) 7.77 (dd, J=8.48, 7.12 Hz, 1H) 7.99 (d, J=8.48 Hz, 1H) 8.60 (m, 1H) 8.96 (dd, J=4.07, 1.36 Hz, 1H) 9.45 (d, J=8.14 Hz, 1H).

Example 63

N'-cyano-N-[1-(3,5-difluorophenyl)ethyl]-2-[2-(trifluoromethyl)phenyl]ethanimidamide

Example 63A ethyl 2-[2-(trifluoromethyl)phenyl]ethanimidoate hydrochloride

The title compound was prepared using the procedure as described in Example 53B, substituting [2-(trifluoromethyl)phenyl]acetonitrile for Example 53A. MS (ESI/NH$_3$) m/z 231 (M+H)$^+$.

Example 63B ethyl N-cyano-2-[2-(trifluoromethyl)phenyl]ethanimidoate

The title compound was prepared using the procedure as described in Example 26B, substituting Example 63A for Example 26A. MS (ESI/NH$_3$) m/z 256 (M+H)$^+$.

Example 63C

N'-cyano-N-[1-(3,5-difluorophenyl)ethyl]-2-[2-(trifluoromethyl)phenyl]ethanimidamide The title compound from was prepared using the procedure as described in Example 26C, substituting Example 63B for Example 26B and substituting 1-(3,5-difluorophenyl)ethylamine for (R)-1-phenylethylamine. MS (ESI/NH$_3$) m/z 367 (M+H)$^+$; $^1$H NMR (DMSO-d$_6$) δ 1.44-1.47 (d, 3H), 4.13 (s, 2H), 5.13-5.18 (m, 1H), 7.10-7.20 (m, 4H), 7.53-7.56 (t, 1H), 7.63-7.66 (t, 1H), 7.78-7.81 (d, 1H), 9.40-9.42 (d, 1H).

(f) Determination of Biological Activity

1. In Vitro Experiments (a) Tissue Culture: Cells of the THP-1 monocytic cell line (American Type Culture Collection, Rockville, Md.) were maintained in the log phase of growth in RPMI medium containing high glucose and 10% fetal calf serum (Invitrogen, Carlsbad, Calif.) according to established procedures (Humphrey B D and Dubyak G R, *J. Immunology* Vol. 157, pages 5627-37 (1996)). Fresh vials of frozen THP-1 cells were initiated for growth every eight weeks. To differentiate THP-1 cells into a macrophage phenotype, a final concentration of 25 ng/ml of lipopolysaccharide (LPS) and 10 ng/ml of IFNγ were added to the cells either for 3 hours for IL-1β release assays.

(b) P2X$_7$ Mediated IL-1β Release: Activation of P2X7 receptors also induces secretion of IL-1β (Verhoef et al., above; Brough et al., *Molecular and Cellular Neuroscience*, Vol. 19, pages 272-280, 2002). THP-1 cells were plated in 24-well plates at a density of 1×10$^6$ cells/well/mL. On the day of the experiment, cells were differentiated with 25 ng/ml LPS and 10 ng/mL final concentration of γIFN for 3 hours at 37° C. Solutions of antagonist compounds were prepared by serial dilutions of a 10 mM DMSO solution of the antagonist into the PBS solution. In the presence of the differentiation media, the cells were incubated with the antagonists of the present invention for 30 minutes at 37° C. followed by a challenge with 1 mM BzATP for an additional 30 minutes at 37° C. Supernatants of the samples were collected after a 5 minute centrifugation in microfuge tubes to pellet the cells and debris and to test for mature IL-1β released into the supernatant using either R & D Systems Human IL-1β ELISA assay or Endogen Human IL-1β ELISA, following the manufacturer's instructions. The maximum IL-1β release at each concentration of test compound was normalized to that induced by BzATP alone to determine the activity of the test compound. Antagonist compounds were tested for activity over a concentration range from 0.001 to 100 μM. Antagonist potency was expressed as the concentration producing a 50% reduction in release of IL-1β or IC$_{50}$. For each experiment, differentiated control cells were also measured over the 60 min time course of the assay to assess background IL-1β accumulation. This non-specific background IL-1β release, typically averaged 3-8% of the maximum BzATP response, was subtracted from the maximum BzATP-induced release and all release values normalized to the BzATP-induced response. Representative compounds of the present invention when tested with the above assay demonstrated antagonist activity at the P2X$_7$ receptor with IC$_{50}$'s equal or less than 10 μM.

(c) P2X$_7$ Mediated Pore Formation. Activation of the P2X$_7$ receptor induces nonspecific pore formation and eventually cell lysis (Verhoef et al., *The Journal of Immunology*, Vol. 170, pages 5728-5738, 2003). Accordingly, the inhibitory activity of the antagonists of the present invention was determined by their capacity to inhibit the agonist-induced pore formation using the fluorescent dye YO-PRO (MW=629) and Fluorometric Imaging Plate Reader (FLIPR, Molecular Devices, Sunnydale, Calif.). Prior to YO-PRO dye addition, the cells were rinsed once in PBS without Mg$^{2+}$ or Ca$^{2+}$ ions, which have been shown to inhibit pore formation (Michel et al., *N-S Arch Pharmacol* 359:102-109, 1999). The YO-PRO iodide dye (1 mM in DMSO) was diluted to a final concentration of 2 μM in phosphate buffered saline (PBS without Mg$^{2+}$ or Ca$^{2+}$) and then placed on the cells prior to the addition of the agonist BzATP. Since the THP-1 cells are a non-adherent cell line, the cells were washed in PBS and loaded with the dye in a conical tube prior to spinning the cells onto poly-lysine-coated black-walled 96-well plates, which were utilized to reduce light scattering. After the addition of the agonist BzATP (50 μM, the EC$_{70}$ value for agonist activation), the YO-PRO dye uptake was observed in the FLIPR apparatus equipped with an Argon laser (wavelength=488 nm) and a CCD camera. The intensity of the fluorescence was captured by the CCD camera every 15 seconds for the first 10 minutes of agonist exposure followed by every 20 seconds for an additional 50 minutes with the data being digitally transferred to an interfaced PC. The exposure setting of the camera was 0.25 sec with an f-stop setting of 2. Solutions of antagonist compounds were prepared by serial dilutions of a 10 mM DMSO solution of the antagonist into the buffer solution with the YO-PRO dye. Antagonist compounds were tested for activity over a concentration range from 0.003 to 100 µM. The test compounds were incubated for 10 minutes with the THP-1 cells at room temperature, after which the cells were stimulated with BzATP and fluorescence measured as described above in the absence of the antagonist. For antagonist activity measurements, the percent maximal intensity was normalized to that induced by 50 µM BzATP and plotted against each concentration of compound to calculate $IC_{50}$ values and account for plate-to-plate variability 2. In Vivo Experiments—Determination of Analgesic Activity Adult male Sprague-Dawley rats (250-300 g), Charles River Laboratories, Portage, Mich. were used in this study. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

(a) Spinal Nerve ligation: A model of spinal nerve ligation-induced neuropathic pain was produced using the procedure originally described by Kim and Chung (Kim and Chung, *Pain, Vol.* 50 pages 355-363, 1992). The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least 1 week and not more than 3 weeks prior to assessment of mechanical allodynia. Mechanical allodynia in the left hind paw was confirmed by comparing the paw withdrawal threshold in grams for the injured left paw and the uninjured right paw. Mechanical allodynia was measured using calibrated von Frey filaments (Stoelting, Wood Dale, Ill.). Rats were placed into inverted individual plastic containers (20×12.5×20 cm) on top of a suspended wire mesh grid, and acclimated to the test chambers for 20 min. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, *Ann. Rev. Pharmacol. Toxicol., Vol.* 20, pages 441-462, 1980). Prior to compound administration, animals demonstrating motor deficit or failure to exhibit subsequent mechanical allodynia were excluded from further studies. The antinociceptive activity of a test compound was determined by comparing its ability to increase the paw withdrawal threshold of the injured left paw relative to vehicle (0%) and the uninjured right paw (100%). Activity of test compounds was determined 60 minutes after an oral dose or 30 minutes after an intraperitoneal dose. Dose-response curves as well as single dose responses were performed. Representative compounds had effective doses ($ED_{50}$'s) equal to or less than 500 µmol/kg.

(b) Complete Freund's adjuvant-induced thermal hyperalgesia: Unilateral inflammation was induced by injecting 150 µL of a 50% solution of complete Freund's adjuvant (CFA) (Sigma Chemical Co., St. Louis, Mo.) in physiological saline into the plantar surface of the right hindpaw of the rat. The hyperalgesia to thermal stimulation was determined 48 hr after CFA injections using a commercially available paw thermal stimulator (UARDG, Department of Anesthesiology, University of California, San Diego, La Jolla, Calif.). Rats were placed individually in Plexiglass cubicles mounted on a glass surface maintained at 30° C., and allowed a 30 min habituation period. A thermal stimulus, in the form of radiant heat emitted from a focused projection bulb, was then applied to the plantar surface of each hind paw. The stimulus current was maintained at 4.5 Amp and the maximum time of exposure was set at 20 sec to limit possible tissue damage. In each test session, each rat was tested in 3 sequential trials at approximately 5 min intervals. Paw withdrawal latencies were calculated as the mean of the two shortest latencies. The antinociceptive activity of a test compound was determined by comparing its ability to increase the paw withdrawal threshold of the injured right paw relative to vehicle (0%) and the uninjured left paw (100%). Activity of test compounds was determined 60 minutes after an oral dose or 30 minutes after an intraperitoneal dose. Dose-response curves as well as single dose responses were performed. Representative compounds had effective doses ($ED_{50}$'s) equal to or less than 500 µmol/kg.

(c) Zymosan Method: Mice were dosed with experimental compounds orally or subcutaneously 30 minutes prior to injection of zymosan. Mice were then injected intraperitonealy with 2 mg/animal of zymosan suspended in saline. Four hours later the animals were euthanized by $CO_2$ inhalation and the peritoneal cavities lavaged with 2×1.5 mL of ice cold phosphate buffered saline containing 10 units of heparin/ml. For IL-1β determination the samples were spun at 10,000×g in a refrigerated microfuge (4° C.), supernatants removed and frozen until ELISAs (Enzyme Linked Immuno-Assay) were performed. ELISAs were performed according to manufacture's instructions. IL-1β was determined relative to vehicle control (Perretti M. et al., *Agents Actions Vol* 35(1-2) pages 71-78 (1992); Torok K, et al., *Inflamm Res. Vol* 44(6) pages 248-252 (1995)). A representative compound of this invention exhibited inhibition of IL-1β release in this assay with an $ED_{50}$ of 90 µmol/kg, sc.

The invention claimed is:

1. A compound of formula (I)

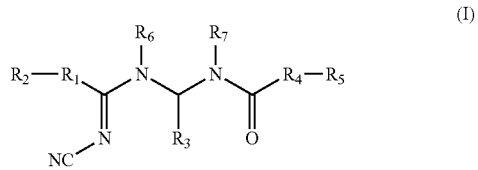

or a pharmaceutically acceptable salt or prodrug thereof, wherein $R_1$ is a bond or a chain selected from the group consisting of alkyl, alkenyl, and alkynyl, $R_2$ is selected from the group consisting of aryl and heteroaryl, wherein aryl and heteroaryl can be independently substituted with 0, 1, 2, or 3 alkenyl, alkyl, alkynyl, halo, haloalkyl, nitro, —C(O)—N—RaRb, —C(O)O—Ra, —C(O)—Ra, —N—RaRb, alkyl-N—RaRb, —O—Ra, —OC(O)—Ra, alkyl-O—Ra, —N—(Ra)—C(O)O—Rb, —N—(Ra)—C(O)N—RaRb, S—Ra, —S(O)—Ra, —S(O)$_2$—Ra, S(O)$_2$—RaRb, wherein Ra and Rb are independently selected from the group consisting of hydrogen, alkyl, haloalkyl, aryl and arylalkyl;

$R_3$ is selected from the group consisting of alkyl and haloalkyl, $R_4$ is alkyl, and $R_5$ is selected from the group consisting of halogen, aryl, and heteroaryl, wherein aryl, and heteroaryl can be independently substituted with 0, 1, 2, 3 or 4 substituents independently selected from alkenyl, alkyl, alkynyl, cyano, halo, haloalkyl, nitro, ethylenedioxy, methylenedioxy, —C(O)NRaRb, —C(O)ORa; —C(O)Ra, —NRaRb, alkylNRaRb, —ORa, —OC(O)Ra, alkylORa, —N(Ra)C(O)ORb, —N(Ra)C(O)NRaRb, SRa, —S(O)Ra, —S(O)$_2$Ra, S(O)$_2$RaRb, wherein Ra and Rb are independently selected from the group consisting of hydrogen, alkyl, haloalkyl, aryl and arylalkyl; and $R_6$ and $R_7$ are independently selected from the group consisting of hydrogen and alkyl.

2. The compound of claim 1, wherein $R_2$ is aryl and $R_5$ is aryl.

3. The compound of claim 2, wherein $R_2$ is phenyl substituted with 0, 1, 2, or 3 substituents selected from the group consisting of alkyl, halo, and haloalkyl, and $R_5$ is selected from the group consisting of naphthyl, phenyl, 1,3-benzodioxolyl and 2,3-dihydro-1,4-benzodioxinyl, wherein $R_5$ can be independently substituted with 0, 1, 2, or 3 halo, —ORa, methylenedioxy, ethylenedioxy, cyano, and —SRa.

4. The compound of claim 3, wherein the compound is selected from the group consisting of N-2-(4-chlorophenyl)-N-(1-{[N-cyano-2-(2-methylphenyl) ethanimidoyl]amino}-2,2-dimethylpropyl)acetamide, N-(1-{[N-cyano-2-(2-methylphenyl)ethanimidoyl] amino}-2,2-dimethylpropyl)-2-(3,4-dimethoxyphenyl) acetamide, N-(1-{[N-cyano-2-(2-methylphenyl)ethanimidoyl] amino}-2,2-dimethylpropyl)-2-(4-methoxyphenyl)acetamide, 2-(1,3-benzodioxol-5-yl)-N-(1-{[N-cyano-2-(2-methylphenyl)ethanimidoyl]amino}-2,2-dimethylpropyl) acetamide N-(1-{[N-cyano-2-(2-methylphenyl)ethanimidoyl] amino}-2,2-dimethylpropyl)-2-(4-cyanophenyl)acetamide, N-(1-{[N-cyano-2-(2-methylphenyl)ethanimidoyl] amino}-2,2-dimethylpropyl)-2-(2,3-dihydro-1,4-benzodioxin-6-yl)acetamide, N-(1-{[N-cyano-2-(2-methylphenyl)ethanimidoyl] amino}-2,2-dimethylpropyl)-2-(1-naphthyl)acetamide, N-(1-{[N-cyano-2-(2-methylphenyl)ethanimidoyl] amino}-2,2-dimethylpropyl)-2-(3,4-difluorophenyl)acetamide N-(1-{[N-cyano-2-(2-methylphenyl)ethanimidoyl] amino}-2,2-dimethylpropyl)-2-[4-(ethylthio)phenyl] acetamide, N-(1-{[N-cyano-2-(2-methylphenyl)ethanimidoyl] amino}-2,2-dimethylpropyl)-2-[4-(methylthio)phenyl] acetamide, N-(1-{[N-cyano-2-(2-methylphenyl)ethanimidoyl] amino}-2,2-dimethylpropyl)-4-(4-methoxyphenyl)butanamide, and N-(1-{[N-cyano-2-(2-methylphenyl)ethanimidoyl] amino}-2,2-dimethylpropyl)-5-phenylpentanamide.

5. The compound of claim 3, wherein $R_1$ is a bond, $R_2$ is phenyl substituted with 0, 1, 2, or 3 substituents selected from the group consisting of alkyl, halo, and haloalkyl, and $R_5$ is selected from the group consisting of naphthyl and phenyl and wherein naphthyl and phenyl are independently substituted with 0, 1, 2, 3 or 4 substituents selected from the group consisting of alkyl, halo, —ORa, —SRa and cyano.

6. The compound of claim 5 that is 2-(4-chlorophenyl)-N-(1-{[(cyanoimino)(2-methylphenyl)methyl]amino}-2,2-dimethylpropyl)acetamide.

7. The compound of claim 1 wherein $R_1$ is alkyl, $R_2$ is aryl and, $R_5$ is heteroaryl.

8. The compound of claim 7 wherein, $R_2$ is phenyl substituted with 0, 1, 2, or 3 substituents selected from the group consisting of alkyl, halo, and haloalkyl, and $R_5$ is selected from the group consisting of quinolinyl, thienyl, and pyridinyl.

9. The compound of claim 8, wherein the compound is selected from the group consisting of N-(1-{[N-cyano-2-(2-methylphenyl)ethanimidoyl] amino}-2,2-dimethylpropyl)-2-quinolin-6-ylacetamide, N-(1-{[N-cyano-2-(2-methylphenyl)ethanimidoyl] amino}-2,2-dimethylpropyl)-2-quinolin-7-ylacetamide, N-(1-{[N-cyano-2-(2-methylphenyl)ethanimidoyl] amino}-2,2-dimethylpropyl)-4-thien-2-ylbutanamide, and N-(1-{[N-cyano-2-(2-methylphenyl)ethanimidoyl] amino}-2,2-dimethylpropyl)-2-pyridin-3-ylacetamide.

10. The compound of claim 1, wherein $R_1$ is alkyl, $R_2$ is aryl, wherein aryl is phenyl substituted with 0, 1, 2, or 3 substituents selected from the group consisting of alkyl, halo, and haloalkyl, $R_4$ is alkyl and, $R_5$ is halogen.

11. The compound of claim 10 that is N-(1-{[N-cyano-2-(2-methylphenyl)ethanimidoyl]amino}-2,2-dimethylpropyl)-2-fluoroacetamide.

12. The compound of claim 1, wherein $R_2$ is heteroaryl and, $R_5$ is aryl.

13. The compound of claim 12, wherein $R_2$ is selected from the group consisting of pyridinyl and quinolinyl.

14. The compound of claim 13, wherein $R_1$ is alkyl, $R_2$ is pyridinyl substituted with 0, 1, 2, or 3 substituents independently selected from the group comprising alkyl, halo, and haloalkyl, and, $R_5$ is phenyl substituted with 0, 1, 2, 3 or 4 substituent independently selected from the group consisting of halogen and alkoxy.

15. The compound of claim 14, wherein the compound is selected from the group consisting of 2-(4-chlorophenyl)-N-(1-{[N-cyano-2-(2-methylpyridin-3-yl)ethanimidoyl]amino}-2,2-dimethylpropyl)acetamide and, N-(1-{[N-cyano-2-(2-methylpyridin-3-yl)ethanimidoyl]amino}-2,2-dimethylpropyl)-2-(3,4-dimethoxyphenyl)acetamide.

16. The compound of claim 1 wherein
$R_2$ is heteroaryl and,
$R_5$ is heteroaryl.

17. The compound of claim 16, wherein
$R_1$ is alkyl,
$R_2$ is pyridinyl and,
$R_5$ is quinolinyl.

18. The compound of claim 17 that is N-(1-{[N-cyano-2-(2-methylpyridin-3-yl)ethanimidoyl]amino}-2,2-dimethylpropyl)-2-quinolin-6-ylacetamide.

19. The compound of claim 13, wherein
$R_1$ is alkyl,
$R_2$ is quinolinyl and,
$R_5$ is phenyl.

20. The compound of claim 19 that is 2-(4-chlorophenyl)-N-(1-{[N-cyano-2-quinolin-5-ylethanimidoyl]amino}-2,2-dimethylpropyl)acetamide.

21. The compound of claim 13 wherein
$R_1$ is a bond,
$R_2$ is quinolinyl and,
$R_5$ is phenyl.

22. The compound of claim 2 that is selected from the group consisting of
N-(1-{[(cyanoimino)(quinolin-5-yl)methyl]amino}-2,2-dimethylpropyl)-2-(3,4-dimethoxyphenyl)acetamide, and 2-(4-chlorophenyl)-N-(1-{[(cyanoimino)(quinolin-5-yl)methyl]amino}-2,2-dimethylpropyl)acetamide.

\* \* \* \* \*